United States Patent [19]

Adams

[11] Patent Number: 5,687,209

[45] Date of Patent: Nov. 11, 1997

[54] AUTOMATIC WARP COMPENSATION FOR LAMINOGRAPHIC CIRCUIT BOARD INSPECTION

[75] Inventor: John A. Adams, Escondido, Calif.

[73] Assignee: Hewlett-Packard Co., Palo Alto, Calif.

[21] Appl. No.: 713,379

[22] Filed: Sep. 13, 1996

Related U.S. Application Data

[63] Continuation-in-part of Ser. No. 419,794, Apr. 11, 1995, Pat. No. 5,583,904.

[51] Int. Cl.$^6$ .................................................. G01N 23/04
[52] U.S. Cl. ................................. 378/22; 378/62; 378/58
[58] Field of Search ........................... 378/62, 57, 58, 378/22, 25, 24, 207, 901; 364/413.1–413.13

[56] References Cited

U.S. PATENT DOCUMENTS

| | | | |
|---|---|---|---|
| 2,292,859 | 8/1942 | Allibone | 250/99 |
| 2,319,350 | 5/1943 | Schiebold | 250/53 |
| 2,511,853 | 6/1950 | Kaiser | 250/62 |
| 2,667,585 | 1/1954 | Gradstein | 250/61.5 |
| 2,720,596 | 10/1955 | Acker | 250/61.5 |
| 2,890,349 | 6/1959 | Huszar | 250/91 |
| 2,998,518 | 8/1961 | Guntert | 250/65 |
| 3,091,692 | 5/1963 | Verse | 250/61.5 |
| 3,149,257 | 9/1964 | Wintermute | 313/60 |
| 3,499,146 | 3/1970 | Richards | 250/61.5 |
| 3,742,229 | 6/1973 | Smith et al. | 250/65 R |
| 3,780,291 | 12/1973 | Stein et al. | 250/363 |

(List continued on next page.)

FOREIGN PATENT DOCUMENTS

| | | | |
|---|---|---|---|
| 0 139 441 | 9/1983 | European Pat. Off. | 23/4 |
| 0225969 | 6/1987 | European Pat. Off. | 31/28 |
| 812792 | 5/1937 | France . | |
| 1138617 | 10/1962 | Germany . | |
| 2946443 | 5/1981 | Germany | 41/16 |
| 143290 | 11/1979 | Japan | 23/18 |
| 60-18833 | 1/1985 | Japan | 11/10 |
| 60-161551 | 8/1985 | Japan | 23/18 |
| 60-196654 | 10/1985 | Japan | 23/18 |
| 61-154645 | 7/1986 | Japan | 6/2 |
| 62-67432 | 3/1987 | Japan | 23/4 |
| 62-116238 | 5/1987 | Japan | 23/4 |
| 868830 | 5/1961 | United Kingdom . | |

OTHER PUBLICATIONS

Hasenkamp, "Radiographic Laminography," *Materials Evaluation*, Aug. 1974, pp. 169–180.

Moler, "Development of a Continuous Scanning Laminograph," Final Report No. IITRI V6034–24, Oct. 1968.

Blanche, "Nondestructive Testing Techniques for Multilayer Printed Wiring Boards," Nondestructive Testing: Trends and Techniques, NASA SP–5082, Oct. 1968, pp. 1–13.

(List continued on next page.)

*Primary Examiner*—Don Wong

[57] ABSTRACT

An improved laminography system with automatic test object warp compensation that allows for generation of high speed and high resolution X-ray laminographs by using a continuous scan method with two or more linear detectors and one or more collimated X-ray sources. Discrete X-ray images, with different viewing angles, are generated by each detector. The discrete X-ray images are analyzed by a computer to generate Z-axis test object warp compensation parameters based upon the location of a pre-determined feature in the test object. The discrete X-ray images are then combined by a computer using the warp compensation parameters to generate laminographic images of different planes in the object under test, or analyzed in such a manner to derive useful data about the object under test. In one embodiment, the improved scanning laminography system does not require any motion of the source or detectors, but simply a coordinated linear motion of the object under test. Higher speed is achieved over conventional laminography systems due to the continuous nature of the scan; the use of pre-determined features located within the test object to determine warp compensation factors; and the ability to generate any plane of data in the object under test without having to re-image the object.

11 Claims, 9 Drawing Sheets

U.S. PATENT DOCUMENTS

| | | | |
|---|---|---|---|
| 3,812,288 | 5/1974 | Walsh et al. | 178/6.8 |
| 3,818,220 | 6/1974 | Richards | 250/61.5 |
| 3,832,546 | 8/1974 | Morsell et al. | 250/315 |
| 3,843,225 | 10/1974 | Kock et al. | 350/3.5 |
| 3,894,234 | 7/1975 | Mauch et al. | 250/358 |
| 3,928,769 | 12/1975 | Smith | 250/445 T |
| 3,962,579 | 6/1976 | Winnek | 250/313 |
| 3,984,684 | 10/1976 | Winnek | 250/313 |
| 4,002,917 | 1/1977 | Mayo | 250/445 T |
| 4,007,375 | 2/1977 | Albert | 250/404 |
| 4,032,785 | 6/1977 | Green et al. | 250/358 T |
| 4,075,489 | 2/1978 | Neal et al. | 250/401 |
| 4,107,563 | 8/1978 | Oddell | 313/60 |
| 4,115,698 | 9/1978 | Hounsfield | 250/445 T |
| 4,130,759 | 12/1978 | Haimson | 250/445 T |
| 4,132,896 | 1/1979 | Klotz et al. | 250/445 |
| 4,139,776 | 2/1979 | Hellstrom | 250/445 T |
| 4,147,933 | 4/1979 | Rougeot et al. | 250/370 |
| 4,179,100 | 12/1979 | Sashin et al. | 250/416 TV |
| 4,211,927 | 7/1980 | Hellstrom et al. | 250/445 |
| 4,228,353 | 10/1980 | Johnson | 250/356 |
| 4,234,792 | 11/1980 | DeCou et al. | 250/361 R |
| 4,260,898 | 4/1981 | Annis | 250/505 |
| 4,287,425 | 9/1981 | Elliot, Jr. | 250/445 T |
| 4,340,816 | 7/1982 | Schott | 250/445 T |
| 4,349,740 | 9/1982 | Grassmann et al. | 378/25 |
| 4,352,021 | 9/1982 | Boyd et al. | 378/12 |
| 4,385,434 | 5/1983 | Zehnpfennig et al. | 29/576 B |
| 4,392,235 | 7/1983 | Houston | 378/10 |
| 4,400,620 | 8/1983 | Blum | 250/363 S |
| 4,411,012 | 10/1983 | Pfeiler et al. | 378/17 |
| 4,414,682 | 11/1983 | Annis et al. | 378/146 |
| 4,415,980 | 11/1983 | Buchanan | 378/58 |
| 4,426,722 | 1/1984 | Fujimura | 378/137 |
| 4,472,824 | 9/1984 | Buckley | 378/34 |
| 4,481,664 | 11/1984 | Linger et al. | 382/8 |
| 4,491,956 | 1/1985 | Winnek | 378/41 |
| 4,516,252 | 5/1985 | Linde et al. | 378/23 |
| 4,521,902 | 6/1985 | Peugeot | 378/138 |
| 4,561,104 | 12/1985 | Martin | 382/8 |
| 4,575,751 | 3/1986 | Duschl | 358/106 |
| 4,614,430 | 9/1986 | Hara et al. | 356/394 |
| 4,618,970 | 10/1986 | Rand et al. | 378/10 |
| 4,628,531 | 12/1986 | Okamoto et al. | 382/8 |
| 4,677,473 | 6/1987 | Okamoto et al. | 358/101 |
| 4,688,241 | 8/1987 | Peugeot | 378/137 |
| 4,688,939 | 8/1987 | Ray | 356/237 |
| 4,707,734 | 11/1987 | Labinger et al. | 358/106 |
| 4,718,075 | 1/1988 | Horn | 378/91 |
| 4,720,633 | 1/1988 | Nelson | 250/310 |
| 4,724,320 | 2/1988 | Ino et al. | 250/307 |
| 4,730,350 | 3/1988 | Albert | 378/10 |
| 4,731,855 | 3/1988 | Suda et al. | 382/8 |
| 4,739,481 | 4/1988 | Yoshitome | 364/414 |
| 4,769,546 | 9/1988 | Kniffler et al. | 250/370.01 |
| 4,803,639 | 2/1989 | Steele et al. | 364/507 |
| 4,809,308 | 2/1989 | Adams et al. | 378/99 |
| 4,852,131 | 7/1989 | Armistead | 378/4 |
| 4,926,452 | 5/1990 | Baker et al. | 378/22 |
| 4,955,045 | 9/1990 | Friede et al. | 378/122 |
| 4,977,328 | 12/1990 | Van Vucht | 250/491.1 |
| 5,012,498 | 4/1991 | Cuzin et al. | 378/22 |
| 5,020,086 | 5/1991 | Peugeot | 378/113 |
| 5,081,656 | 1/1992 | Baker et al. | 378/21 |
| 5,097,492 | 3/1992 | Baker et al. | 378/22 |
| 5,199,054 | 3/1993 | Adams et al. | 378/21 |
| 5,259,012 | 11/1993 | Baker et al. | 378/21 |
| 5,291,535 | 3/1994 | Baker et al. | 378/22 |
| 5,465,152 | 11/1995 | Bilodeau et al. | 356/371 |
| 5,491,737 | 2/1996 | Yarnall et al. | 378/58 |
| 5,500,886 | 3/1996 | Duff | 378/58 |
| 5,592,562 | 1/1997 | Rooks | 378/62 |
| 5,594,770 | 1/1997 | Bowles et al. | 378/58 |

OTHER PUBLICATIONS

Hamre, "Nondestructive Testing Techniques for Muitilayer Printed Wiring Boards," Report No. IITRI–E6024–15, Sep. 1965.

Kruger et al., "Industrial Applications of Computed Tomography at Los Alamos Scientific Labratory," LA–8412–MS, Jun. 1980.

Stanley et al., "A New NDE Capability for Thin–Shelled Structures," AFWAL–TR–84–4120, Materials Lab, Wright Patterson AFB, Sep. 1984.

Deane et al., IRT Corp., "Using X–Ray Vision to Verify SMD–Board Quality," Electronics Test, Feb. 1987, pp. 32–35.

Soron, IRT Corp., "X–Ray Inspection Meets Increased PWB Throughput, Density Challenge–Part 1", Electronics, Oct. 1987, pp.36–37.

Pound, "Image Processing Boosts the Power of Non–destructive Testing," Electronic Packaging and Production, Jun. 1985.

Casey, "X–Ray Inspection," Manufacturing Systems, Jul. 1987, p. 18ff.

Corey, IRT Corp., "Artificial Perception Gives Super Vision," Research and Development, Oct. 1984.

LaClair, "Nondestructive Measurement and Inspection Process," IBM Technical Discclosure Bulletin, vol. 18, No. 12, May 1976.

Hufault et al., "Lead–Indium Solder Joint Analysis," IBM Technical Disclosure Bulletin, vol. 19, No. 11, Apr. 1977.

Wittenberg, "IRT Improves SMT X–Ray Inspection System," Electronic Engineering Times, Oct. 5, 1987, p. 53.

Phelps, Christi, "Four Pi Captures Contact, Capital; Unveils Product," San Diego Business Journal, Week of Oct. 10–16, 1888.

Smith, Steven W. and Kruger, Robert A., "Fast Circular Tomography Device for Cardiac Imaging: Image Deflection Mechanism and Evaluation", IEEE Transactions on Medical Imaging, vol. MI–6, No. 2, Jun. 1987.

Four Pi Systems product brochure for "3DX Series 2000" Automated Inspection System, Copyright 1988.

Juha, Mike, "Automated Inspection of Surface Mounted Device Solder Connections", Proceedings of Soldering Technology Seminar—19–20 Feb. 1985, Naval Weapons Center, China Lake, CA, Publication NWC TS 85–25, pp. 73–90.

Smith, Charles R. and Erker, Joseph W., "Low cost, high resolution x–ray detector system for digital radiography and computed tomography", SPIE vol. 2009 X–Ray Detector Physics and Applications II, 1993 pp. 31–35.

D. Meyer–Ebrecht and H. Weiss, "Tomosynthesis—3–D X–ray imaging by means of holography or electronics", OPTICA ACTA, vol. 24, No. 4, 1977, pp. 293–303.

Kolitsi et al., "A multiple projection method for digital tomosynthesis", Med. Phys., vol. 19, No. 4, Jul./Aug. 1992, pp. 1045–1050.

Haaker et al., "Digital angiographic tomosynthesis with fewer artifacts", Med. Phys., vol. 12, No. 4, Jul./Aug. 1985, pp. 431–436.

Kruger et al., "Reconstruction of blood vessels from x–ray substraction projections: Limited angle geometry", Med. Phys., vol. 14, No. 6, Nov./Dec. 1987, pp. 940–948.

Baranov et al., "System of Digital Tomosyntheis for Nondestructive Testing", *Plenum Publishing Corporation* 0038–5492/88/2405, 1989, pp. 321–327.

Vainberg et al., "Reconstruction of the Internal Three–Dimensional Structure of Objects Based on Real–Time Integral Projections", *Plenum Publishing Corporation* 0038–5492/81/1706, 1982, pp. 415–423.

J. Zhou et al., "Computed Laminography for materials testing", 1996 American Institute of Physics, Appl. Phys. Lett. 68(24) 10 Jun. 1996.

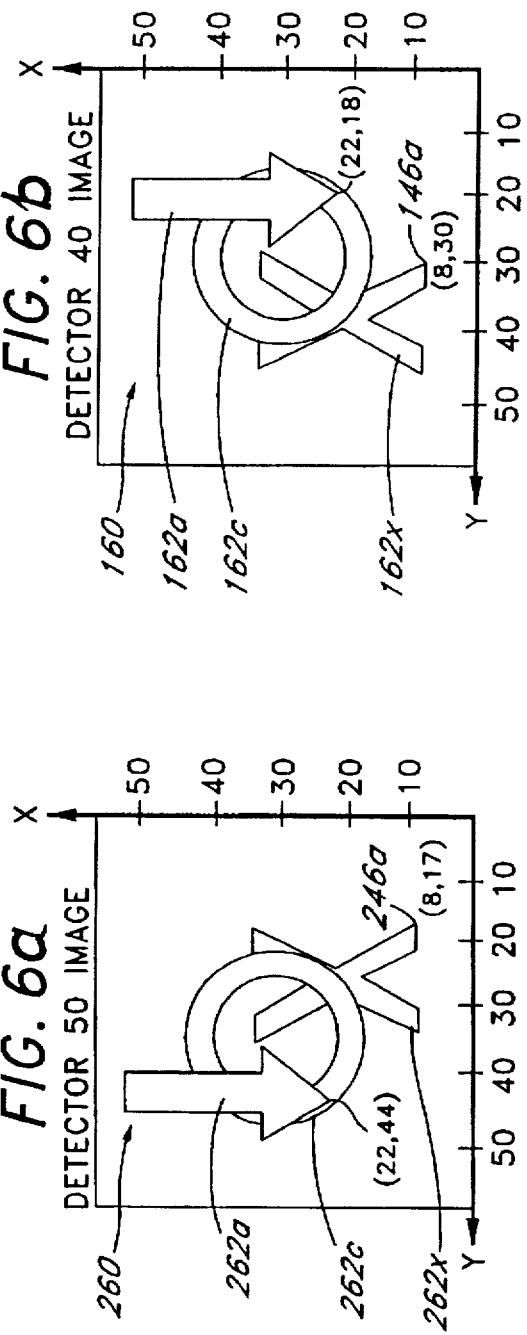
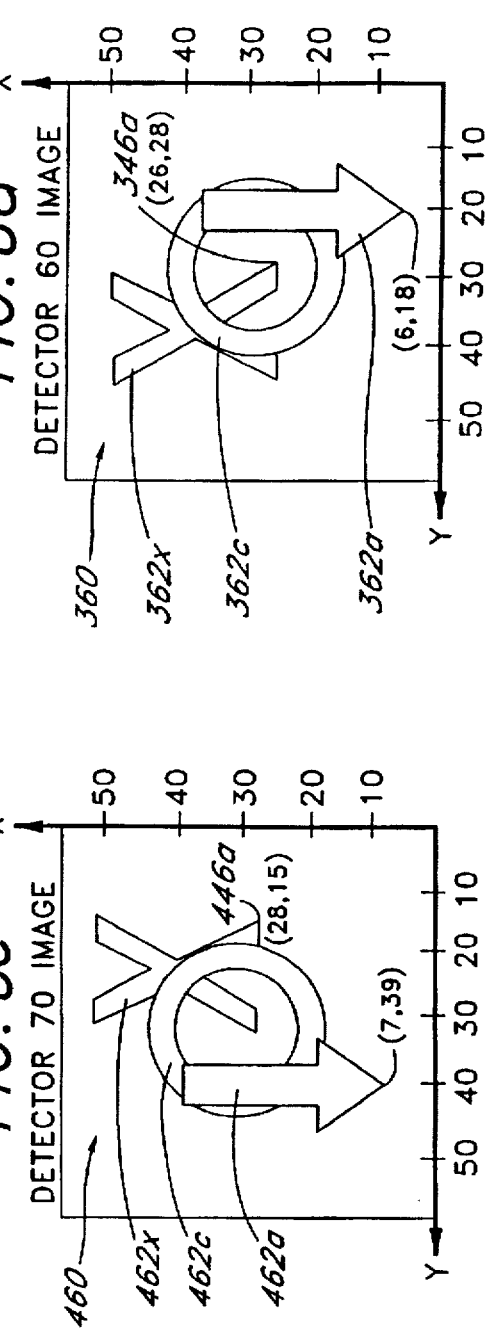

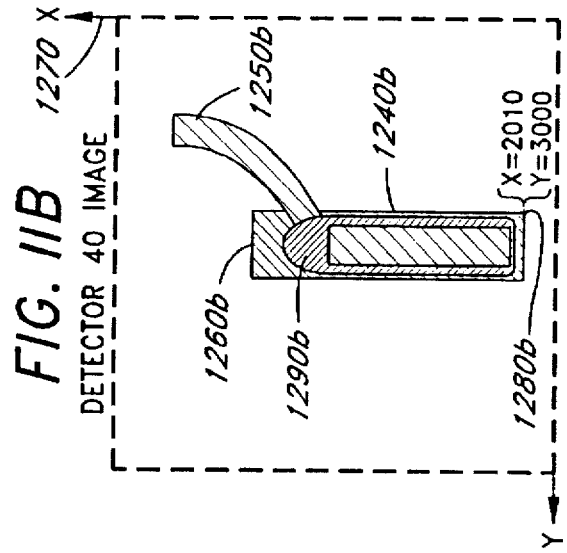
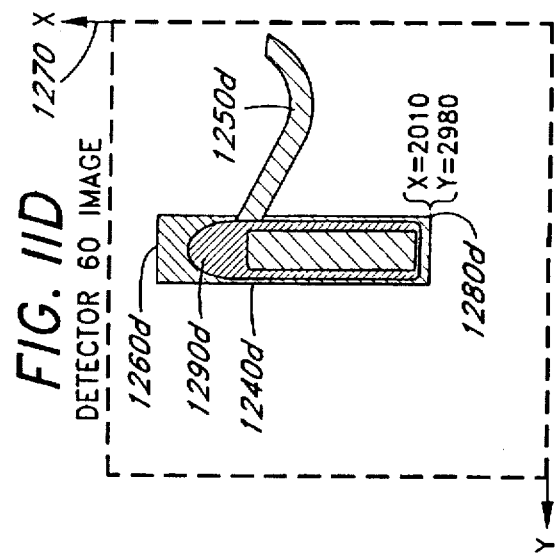
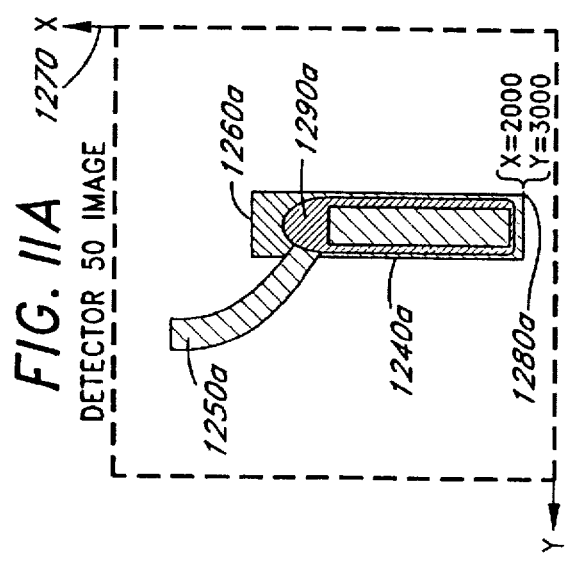
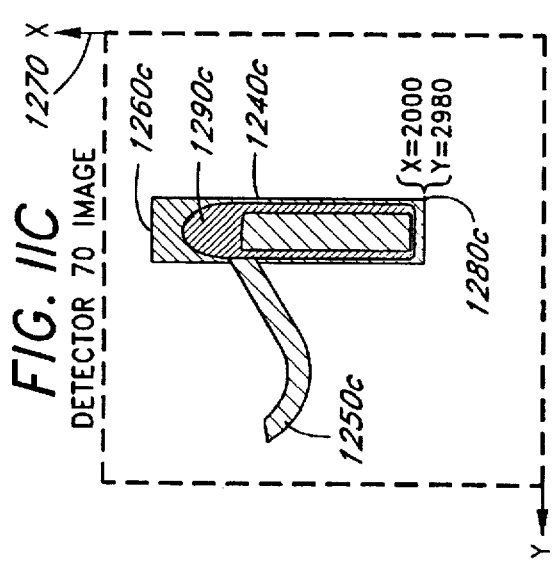

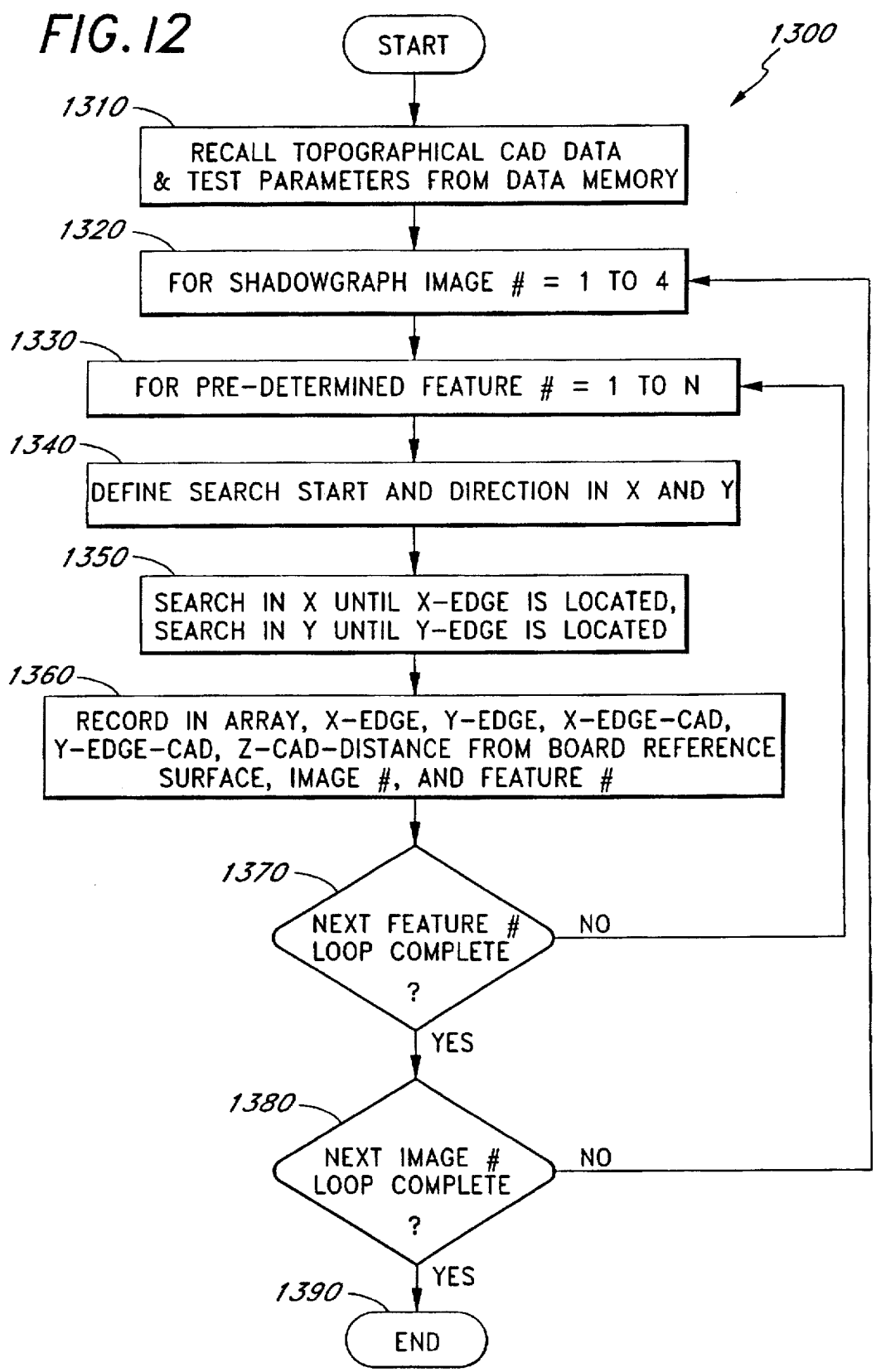

AUTOMATIC WARP COMPENSATION FOR LAMINOGRAPHIC CIRCUIT BOARD INSPECTION

RELATED APPLICATION

This application is a continuation-in-part of patent application Ser. No. 08/419,794, filed Apr. 11, 1995, by inventor John A. Adams, and entitled "CONTINUOUS LINEAR SCAN LAMINOGRAPHY SYSTEM AND METHOD" now U.S. Pat. No. 5,583,904.

FIELD OF THE INVENTION

The invention relates to computerized laminography, and in particular, to systems which incorporate automatic compensation for warpage of the test object.

BACKGROUND OF THE INVENTION

Laminography techniques are widely used to produce cross sectional images of selected planes within objects. Conventional laminography requires a coordinated motion of any two of three main components comprising a laminography system, that is, a radiation source, an object being inspected, and a detector. The coordinated motion of the two components can be in any of a variety of patterns including but not limited to: linear, circular, elliptical or random patterns. Regardless of which pattern of coordinated motion is selected, the configuration of the source, object, and detector is such that any point in the object plane is always projected to the same point in the image plane and any point outside the object plane is projected to a plurality of points in the image plane during a cycle of the pattern motion. In this manner, a cross sectional image of the desired plane within the object is formed on the detector. The images of other planes within the object experience movement with respect to the detector thus creating a blur background on the detector upon which is superimposed the sharp cross sectional image of the desired focal plane within the object. Although any pattern of coordinated motion can be used, circular patterns are generally preferred because they are more easily produced.

U.S. Pat. No. 4,926,452 entitled "AUTOMATED LAMINOGRAPHY SYSTEM FOR INSPECTION OF ELECTRONICS", issued to Baker et al. describes a continuous circular scanned laminography system wherein the object remains stationary while the X-ray source and detector move in a coordinated circular pattern. The moving X-ray source comprises a microfocus X-ray tube wherein an electron beam is deflected in a circular scan pattern onto an anode target. The resulting motion of the X-ray source is synchronized with a rotating X-ray detector that converts the X-ray shadowgraph into an optical image so as to be viewed and integrated in a stationary video camera, thus forming a cross sectional image of the object. A computer system controls an automated positioning system that supports the item under inspection and moves successive areas of interest into view. In order to maintain high image quality, a computer system also controls the synchronization of the electron beam deflection and rotating optical system, making adjustments for inaccuracies of the mechanics of the system.

Laminographic cross sectional images may also be formed within the data memory of a computer by combining two or more individual images that were formed with coordinated positioning of two of the three main components comprising the laminography system, that is, a source, an object, and a detector. The images are combined within the computer memory such that any point in the object focal plane in one image is always combined with the same point in the object focal plane of another image, this other image consisting of a different angular view of the same object. If the individual views are taken with the detector describing a circular path, then the combined image formed from the individual images approaches the appearance of a continuous circular scanned image (as described in U.S. Pat. No. 4,926,452, discussed above) when the number of individual images is very large. Mathematically shifting the pixel combinations of the multiple individual images has the result of changing the location of the focal plane in the object. Thus, this method of generating a cross sectional image of an object has the advantage over moving and blurring methods, in that from one set of images, multiple laminographic cross sectional images of different focal planes may be formed. This technique has been called synthetic laminography, or computerized synthetic cross sectional imaging.

The laminography techniques described above are currently used in a wide range of applications including medical and industrial X-ray imaging. Laminography is particularly well suited for inspecting objects which comprise several layers having distinguishable features within each layer. However, some previous laminography systems which produce such cross sectional images typically experience shortcomings in resolution and/or speed of inspection, thus accounting for its rare implementation. These shortcomings are frequently due to the difficulties in achieving high speed coordinated motion of the source and detector to a degree of precision sufficient to produce a high resolution cross sectional image.

In a laminography system which views a fixed object and has a field of view which is smaller than the object being inspected, it may be necessary to move the object around within the field of view thus generating multiple laminographs which, when pieced together form an image of the entire object. This is frequently achieved by supporting the object on a mechanical handling system, such as an X,Y,Z positioning table. The table is then moved to bring the desired portions of the object into the field of view. Movement in the X and Y directions locates the area to be examined, while movement in the Z direction moves the object up and down to select the plane within the object where the cross sectional image is to be taken. While this method effectively enables various areas and planes of the object to be viewed, there are inherent limitations associated with the speed and accuracy of such mechanical motions. These constraints effectively act to increase the cycle time, thereby reducing the rates at which inspection can occur. Furthermore, these mechanical motions produce vibrations which tend to reduce the system resolution and accuracy.

U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al. describes a system which enables multiple locations within an object to be imaged without mechanical movement of the object. The object is interposed between a rotating X-ray source and a synchronized rotating detector. A focal plane within the object is imaged onto the detector so that a cross sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions.

Deflection voltage signals are applied to the X and Y deflection coils and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged. Changes in the radius of the X-ray source path result in a change in the Z level of the imaged focal plane. This system solves many of the problems of the early laminography systems in the generation of high resolution and high speed cross sectional images. This system is an improvement over that described in U.S. Pat. No. 4,926,452 in that it allows for the inspection of objects that are larger than the field of view by electronically generating cross sectional images off-axis to the rotation of the source and detector, thus eliminating a major source of mechanical motion. Additionally, the selection of the focal plane is accomplished by electronically sizing the diameter of the circular scan, thus eliminating the mechanical Z motion from the system described in U.S. Pat. No. 4,926,452. The method of generating cross sectional images described in U.S. Pat. No. 5,259,012 can theoretically go twice as fast as the system described in U.S. Pat. No. 4,926,452, since it does not have to wait for mechanical motion. It does have the same limitations as the system described in U.S. Pat. No. 4,926,452 as to source power and spot size limitations. Thus, total inspection speed is only a two to three times improvement, while adding considerable complexity in electronic circuitry and calibration efforts. While the system described in U.S. Pat. No. 5,259,012 does not require an X, Y, or Z table to position the object under inspection, it still needs a very complex and large X-ray tube to enable the system to work. The diameter of the X-ray tube must be slightly larger than the largest horizontal dimension of the object to be inspected with cross sectional imaging. Otherwise, the object, or the detector and X-ray tube, must be moved in the X direction and/or the Y direction, to inspect the entire object. Another disadvantage of this system is the requirement that the rotary detector imaging system relies on spinning a mechanical assembly at 600 or more revolutions per minute (RPM).

U.S. Pat. No. 5,020,086 entitled "MICROFOCUS X-RAY SYSTEM", issued to Peugeot discloses a system for tomosynthesis wherein an object is scanned by an X-ray beam from a circular position on a target resulting from the electron beam being scanned in a circle by appropriate control signals from a beam controller and applied to the deflection coils of a microfocus X-ray tube. Tomosynthesis is accomplished by the well known method of in-register combination of a series of digital X-ray images produced by X-ray beams emanating from different locations. This is achieved by positioning an X-ray source at multiple points on a circle around a central axis. This system eliminates some of the mechanical motion required by the system described in U.S. Pat. No. 4,926,452, in that the detector does not have to rotate. However, practical limitations of pixel size and resolution tend to limit the Peugeot system to inspection of items with small fields of view. Additionally, the system still requires an X,Y table to position the object under the field of view. The speed of a commercial prototype of this system is not significantly faster than the system described in U.S. Pat. No. 5,259,012, but may have a slightly lower cost of manufacture.

While there has been some well received commercial success of the system described in U.S. Pat. No. 4,926,452, and some commercial interest in both the system described in U.S. Pat. No. 5,020,086 and the system described in U.S. Pat. No. 5,259,012, industry still desires a cross sectional inspection system which operates at an even higher inspection speed while costing less than the existing industrial cross sectional inspection systems. If a new cross sectional imaging system could meet the demands of low cost and high performance, the commercial applications and usage would grow rapidly over the current technology and the benefit to the electronics industry for circuit board inspection would be greatly increased.

The above discussed references disclose devices and methods for the generation of cross-sectional images of test objects at a fixed or selectable cross-sectional image focal plane. In these systems, an X-ray source system and an X-Ray detector system are separated in the "Z" axis direction by a fixed distance and the cross-sectional image focal plane is located at a predetermined specific position in the "Z" axis direction which is intermediate the positions of the X-ray source system and the X-ray detector system along the "Z" axis. The X-Ray detector system collects data from which a cross-sectional image of features in the test object, located at the cross-sectional image focal plane, can be formed. All of these systems postulate that the features desired to be imaged are located in the fixed or selectable cross-sectional image focal plane at the predetermined specific position along the "Z" axis. Thus, in these systems, it is essential that the positions of the cross-sectional image focal plane and the plane within the object which is desired to be imaged, be configured to coincide at the same position along the "Z" axis. If this condition is not met, then the desired image of the selected feature within the test object will not be acquired. Instead, a cross-sectional image of a plane within the test object which is either above or below the plane which includes the selected feature will be acquired.

Presently, one technique commonly used for positioning the selected feature of the test object within the cross-sectional image focal plane physically measures the "Z" axis position of the selected feature. Using this measurement, the test object is then positioned along the "Z" axis such that the selected feature coincides with the "Z" axis position of the cross-sectional image focal plane. Any of a variety of standard methods and instruments may be used to physically measure the "Z" axis position of the selected feature of the test object. There are several types of commercially available Z-ranging systems which are used to determine the distance between a known location in "Z" and a feature on the surface, or just below the surface, of the test object. Such systems are as simple as mechanical fixturing of the test object, a mechanical probe, a laser based optical triangulation system, an optical interferometric system, an ultrasonic system, or any other type of measuration device that is suitable. Any one of these "Z" distance measuring systems is typically used to form a "Z-map" of the surface of the test object. The Z-map typically consists of an X and Y array of the Z-values of the surface of the test object. The (X,Y) locations being points on a plane of the test object which are substantially parallel to the cross-sectional image focal plane. The systems most commonly used in systems for cross-sectional image formation of features on circuit boards have been laser based triangulation range finders.

Range finders have been used in particular for cross-sectional X-ray image systems that are used to image electronic circuit board assemblies. Circuit board assemblies are typically very thin in comparison to the surface area in which the components are mounted. Some circuit assemblies are made with very dimensionally stable material, such as ceramic substrates. However, the majority of circuit board assemblies are constructed with board material that is somewhat flexible or in some cases very flexible. This flexibility allows the board to develop a warp in the axis perpendicular to the major surface areas. Additionally, some circuit board assemblies have variations in board thickness. Besides electronic assemblies, there are many other objects that have dimensional variation on the scale that is significant when compared to the depth of field of the "Z" focal plane in cross-sectional X-ray imaging. By measuring the surface of a warped test object, means can then often be used to properly adjust the positional relationship of the test object with respect to the "Z" focal plane of the cross-sectional imaging system so that the desired image of the features of interest within the test object can be imaged.

Specifically, one such range finder system is designed for use in a system such as that described in U.S. Pat. No. 4,926,452 to Baker, et al.. Baker et al. discloses a laminography system in which an X-ray based imaging system having a very shallow depth of field is used to examine solid objects such as printed circuit cards. The shallow depth of field provides a means for examining the integrity of a solder joint without interference from the components above and below the solder joint. The material above and below the solder joint is out of focus, and hence, contributes to a more or less uniform background. To provide the needed selectivity, the depth of field of the laminographic imaging system is on the order of approximately less than 2 mils. Unfortunately, surface variations on the printed circuit card often exceed this tolerance. To overcome this drawback, the surface of the printed circuit card is mapped using a laser range finder. The detailed laser range finder map is then used to position the circuit card with respect to X-ray imaging system such that the component of interest is in focus even when the card is translated from one field of interest to another.

The disadvantage of most laser ranging systems is that they require that the surface being mapped be free of imperfections which have dimensions on the order of those of the diameter of the laser beam. Two types of commercially available ranging systems are often used. Both types operate by illuminating the point on the surface with a collimated beam of light from a laser. In the first type of system, the laser beam strikes the surface at right angles to the surface and illuminates a small spot on the surface. The illuminated spot is imaged onto an array of detectors by a lens. The distance from the laser to the surface determines the degree to which the illuminated spot is displaced from the axis of the lens. As a result, as the distance changes, the image of the spot moves along the array of detectors. The identity of the detector on which the projected spot falls provides the information needed to determine the distance to the point on the surface. In this type of system, an imperfection that is larger than the laser beam at the point of measurement will result in an error that can be as large as the height of the imperfection. In more sophisticated versions of this type of system, the image of the laser spot falls on more than one detector. The detection circuitry computes the center of the image to provide a more precise distance determination. Here, imperfections in the surface that distort the image on the detector array will also cause errors even though the height of the imperfection is insufficient to cause a significant distance error. The second type of system assumes that the surface is flat and reflective. In this type of system, the laser beam is directed at the surface of the circuit board at an oblique angle and reflected from the surface onto the detector array without an imaging lens. The distance is then measured by identifying the detector receiving the reflected light beam. The distance measurement relies on a knowledge of the angle of incidence of the laser beam with respect to the surface. If the surface includes an imperfection which has dimensions similar to that of the laser beam, this assumption will not be satisfied, since the surface of the imperfection will determine the angle of incidence. The resulting errors can be much larger than the height of the imperfection in this type of system. In principle, the problems introduced by such imperfections could be mitigated by increasing the diameter of the laser beam. Unfortunately, the diameter of the laser beam must be kept to a minimum to provide the required accuracy in the range measurement.

In spite of the obvious advantage to measuring the warp of test objects so that the desired features of the test object can be accurately imaged, existing techniques in the art have certain less desirable features. One drawback of the existing methods is the time or the equipment complexity that it takes to generate the Z-map. For each point, something must be moved, the test object relative to the position of the range finder, or the beam of the range-finder relative to the test object in a complex self-scanning laser range-finder system. This added time or equipment complexity affects the overall cost of the imaging system in either the up-front costs of the complex scanning-laser range finder system, or in the extra time it takes to form the Z-map in more conventional laser range finder systems.

Another disadvantage of existing Z-map systems is the possibility that the desired features to be measured are not in strict mechanical relationship to the surface Z-map of the test object. This can occur, for example, when the desired feature to be imaged is on the opposite side, from the Z-map surface, of a double-sided circuit board assembly that has a significant variation in board thickness. To compensate for this effect, existing cross-sectional imaging systems would have to generate a Z-map of both sides of a test object at added time and complexity. There is also the possibility that the feature to be imaged in the test object is internal to the test object at a "Z" distance from the "Z-map" surface of the board, with significant variation in this distance from board to board or within the same board.

Accordingly, several objects and advantages of the present invention are that it provides an improved, lower cost, and simpler way to achieve high speed and high resolution cross sectional imaging for the inspection of electrical connections, than do previous systems.

It is one object of the present invention to eliminate the costly and complex scanned beam type X-ray tube used in U.S. Pat. Nos. 5,020,086 and 5,259,012, and replace the scanned beam X-ray tube with a standard low cost X-ray system.

It is another object of the present invention to eliminate the expensive X, Y positioning table (U.S. Pat. No. 5,020,086) or the X, Y, Z table (U.S. Pat. No. 5,259,012) with a low cost, single axis, highly reliable, continuous motion system.

It is another object of the present invention to replace the large diameter, expensive, and highly complex X-ray tube and system used in the U.S. Pat. No. 5,259,012 system, with a standard low cost X-ray system.

It is another object of the present invention to replace the complex rotating detector systems described in U.S. Pat. Nos. 4,926,452 and 5,259,012, and the large diameter and expensive vacuum tube detector disclosed in U.S. Pat. No. 5,020,086, with conventional, highly reliable, solid state, mass produced, low cost, high performance, linear line scan type detectors.

It is yet another object of the present invention to replace the Z-map systems used in the prior art, for example, laser range finding systems, with a system that automatically compensates for test object warpage without requiring additional system hardware over that hardware which is required to form the X-ray laminographic cross-sectional image.

It is a further object of the present invention to replace the Z-map systems used in the prior art with a system that automatically compensates for test object warpage and that operates at a substantially improved speed over existing systems without requiring additional system hardware over that hardware which is required to form the X-ray cross-sectional image nor requiring additional system motion to form the Z-map.

SUMMARY OF THE INVENTION

The present invention comprises a greatly improved computerized laminography system which incorporates automatic compensation for warpage of the test object. In one embodiment, the present invention uses a continuous scan method for high speed, high resolution X-ray inspection of solder joints on printed circuit boards. The system does not require motion of the detector, the X-ray tube, the spot of X-rays, or the beam of X-rays. The only motion required is a smooth linear motion of the object to be imaged. The invention compensates for warpage of the printed circuit board by analyzing the X-ray image data acquired by the system. Thus, no additional hardware is required. The present invention is faster than previous laminography systems for the inspection of electrical connections on a circuit board.

Circuit boards are fed into the X-ray laminography scanner at a rate of approximately 0.3 inches per second at a uniform velocity. The circuit boards are separated from each other by approximately 0.7 inches. The mechanism that provides the uniform linear motion is a moving chain belt that supports the circuit boards on their two opposite parallel sides.

The detector system includes a minimum of two (2) linear scanner detectors (preferably four (4) linear scanner detectors) symmetrically positioned at an angular relationship to the circuit board. The linear scanner detectors are mounted so that they are very close to the bottom of the board under test. Each linear scanner detector has a thin deposit of X-ray sensitive phosphor on the detector surface and achieves approximately 16 lp/mm resolution. Additionally, each linear scanner detector has built in electronics to provide an 8 to 16 bit data stream with digitizing electronics that interface directly to a personal computer (PC).

The X-ray source includes at least one source of X-rays (preferably two) collimated so that each X-ray tube gives off two fan beams of X-rays. The X-ray sources are mounted with respect to the circuit board to provide the preferred laminographic angle and at the preferred distance from the circuit board and linear scanner detectors such that the combination of their spot size and the board to detector standoff and X-ray power available all cooperate to provide a high resolution image on the detector having adequate light levels. The preferred source is a standard X-ray tube capable of operating at 125 kilovolts (KV) with an anode current in the range of approximately 0.1 milliamperes (ma) to 1.0 milliamperes. If two tubes are used, both tubes may be powered by a single high voltage (HV) power supply. The preferred focal spot size of the X-ray tube is in the range of approximately 100 microns to 1000 microns in diameter.

The data from each linear scanner detector is used to generate, within computer memory, a complete X-ray picture of the 8.5"×12" circuit board. In a 4 detector system, the minimum memory requirement is approximately 260 megabytes. For the system to analyze one circuit board while another image of a second circuit board is acquired requires an additional 260 megabytes of memory. Thus, a total of 520 megabytes of memory is required for a system having four linear scanner detectors and that acquires one set of four images while the previously acquired set of four images is being analyzed. It is preferred to have the computer memory designed in such a way that it can be switched over to the detectors for image gathering, then switched to a view analysis computer for generation of the slice image or images for analysis, however this is not essential.

The computer includes an automated Z-axis warp compensation mode of operation wherein pre-determined specific features in the four separate images are located and positions of the pre-determined features are determined or measured in the X and Y directions by means of a view analysis processor and associated software algorithms. The positions of these pre-determined features are then used to generate warp compensation parameters and/or a warp compensation map by means of the view analysis processor and an associated computer algorithm. The warp compensation parameters include a data array in X and Y which contains pixel shifts in X and Y and the design distance of the pre-determined specific feature from the top reference surface of the test object or circuit board. In this manner, the generation of a Z-map, which includes an array in X and Y of the Z distances of the surface of the board from a known Z reference, is not required. However, generation of a Z-map from the warp compensation parameters is a straightforward matter.

Laminographic slices, i.e., images, of a specific Z-axis plane are generated by combining the four separate images by shifting the pixel locations in X and Y to correspond to a specific Z-axis focal plane in the object, corrected as required in accordance with the warp compensation parameters. Any number of focal planes may be generated from a single set of four images by this process.

The laminographic images are then analyzed in a conventional way to yield data about the quality of the electrical connection on the circuit board.

In a first embodiment, the invention is an imaging system comprising: a first X-ray source; a first linear X-ray detector positioned to intercept X-rays emitted by the first X-ray source at a first angle; a second linear X-ray detector positioned to intercept X-rays emitted by the first X-ray source at a second angle; a linear motion system positioned between the first X-ray source and the first and second linear X-ray detectors, the linear motion system further having a support for an object under test, the linear motion system configured to transport the object under test through the X-rays emitted at the first angle and the second angle and detected by the first linear X-ray detector and the second linear X-ray detector, respectively, after having passed through the object under test, thereby forming a first shadowgraph image and a second shadowgraph image of the object under test; and a control system connected to the linear motion system, the first linear X-ray detector and the second linear X-ray detector, wherein the control system regulates the linear motion system and the formation of the first and second shadowgraph images to produce a laminographic cross sectional image of a cutting plane of the object under test, wherein the position of the cutting plane is accurately determined by the control system by generation or measurement of Z-axis warp compensation parameters. This embodiment may further comprise a first collimator positioned with respect to the first X-ray source such that the first collimator is configured to direct X-rays emitted by the first X-ray source toward the first linear X-ray detector and to block X-rays travelling in other directions. Additionally, this imaging system may further comprise a second collimator positioned with respect to the first X-ray source such that the second collimator is configured to direct X-rays emitted by the first X-ray source toward the second linear X-ray detector and to block X-rays travelling in other directions. In some configurations, the imaging system further comprises a second X-ray source laterally positioned with respect to the first X-ray source; a third linear X-ray detector positioned to intercept X-rays emitted by the second X-ray source at a third angle; and a fourth linear X-ray detector positioned to intercept X-rays emitted by the second X-ray source at a fourth angle. In certain configurations, the imaging system further comprises a third collimator positioned with respect to the second X-ray source such that the third collimator is configured to direct X-rays emitted by the second X-ray source toward the third linear X-ray detector and to block X-rays travelling in other directions. Similarly, a fourth collimator may be positioned with respect to the second X-ray source such that the fourth collimator is configured to direct X-rays emitted by the second X-ray source toward the fourth linear X-ray detector and to block X-rays travelling in other directions. The first, second, third and fourth linear X-ray detectors may further comprise monolithic, self-scanning, linear, photodiode arrays. Additionally, an X-ray scintillation material may be deposited on the first, second, third and fourth linear photodiode array X-ray detectors. The X-ray scintillation material further comprise gadolinium oxysulfide. The linear motion system in some configurations comprises a conveyor belt.

In a second embodiment, the invention is an apparatus for producing cross sectional images of a cutting plane within an object comprising: a linear motion system adapted to support and transport an object under test along a substantially linear path; a first source of X-rays for producing X-rays, the first source of X-rays positioned adjacent to the linear motion system such that the X-rays produced by the first X-ray source impinge upon a first surface of the object and scan the object as the linear transport system moves the object along the linear path; a first linear X-ray detector comprising a plurality of X-ray detector elements positioned adjacently in a substantially linear fashion, the first linear X-ray detector positioned adjacent a second surface of the object substantially opposite the first surface, the first linear X-ray detector thereby intercepting and detecting X-rays which enter the object through the first surface and exit the object through the second surface, the first linear X-ray detector positioned at a first angle with respect to the first source of X-rays; a first linear X-ray detector readout control system, the first linear X-ray detector readout control system further having a clock which controls the periodic reading and storing of signals produced by the plurality of X-ray detector elements; a second linear X-ray detector positioned a distance away from the first linear X-ray detector, the second linear X-ray detector comprising a plurality of X-ray detector elements positioned adjacently in a substantially linear fashion, the second linear X-ray detector positioned adjacent the second surface of the object substantially opposite the first surface, the second linear X-ray detector thereby intercepting and detecting X-rays which enter the object through the first surface and exit the object through the second surface, the second linear X-ray detector positioned at a second angle with respect to the first source of X-rays; a second linear X-ray detector readout control system, the second linear X-ray detector readout control system further having a clock which controls the periodic reading and storing of signals produced by the plurality of X-ray detector elements; a control system which controls and coordinates the operation of the linear motion system and the first and second linear X-ray detector readout control systems such that the first linear X-ray detector produces a first X-ray shadowgraph image of the object and the second linear X-ray detector produces a second X-ray shadowgraph image of the object; and an image analysis system which receives the first and second X-ray shadowgraph images of the object and combines the first and second X-ray shadowgraph images of the object to form a cross sectional image of a cutting plane of the object, wherein the position of the cutting plane is accurately determined by the image analysis system by generation or measurement of Z-axis warp compensation parameters. In some configurations, the apparatus further comprises a first collimator positioned with respect to the first source of X-rays such that the first collimator is configured to direct X-rays emitted by the first source of X-rays toward the first linear X-ray detector and to block X-rays travelling in other directions. Similarly, a second collimator may be positioned with respect to the first source of X-rays such that the second collimator is configured to direct X-rays emitted by the first source of X-rays toward the second linear X-ray detector and to block X-rays travelling in other directions. In some configurations, this apparatus further comprising a second source of X-rays laterally positioned with respect to the first source of X-rays; a third linear X-ray detector positioned to intercept X-rays emitted by the second source of X-rays at a third angle; and a fourth linear X-ray detector positioned to intercept X-rays emitted by the second source of X-rays at a fourth angle. Similarly, a third collimator may positioned with respect to the second source of X-rays such that the third collimator is configured to direct X-rays emitted by the second source of X-rays toward the third linear X-ray detector and to block X-rays travelling in other directions a fourth collimator may be positioned with respect to the second source of X-rays such that the fourth collimator is configured to direct X-rays emitted by the second source of X-rays toward the fourth linear X-ray detector and to block X-rays travelling in other directions. In some configurations, the first, second, third and fourth linear X-ray detectors further comprise monolithic, self-scanning, linear, photodiode arrays. An X-ray scintillation material may be deposited on the first, second, third and fourth linear photodiode array X-ray detectors. In some embodiments, the X-ray scintillation material further comprises gadolinium oxysulfide. The linear motion system may comprise a conveyor belt.

In a third embodiment, the invention is a method of producing a cross sectional image of an object comprising the steps of: providing a first source of X-rays; detecting X-rays produced by the first source of X-rays with a first linear X-ray detector after the X-rays have impinged upon and penetrated the object from a first angular orientation; detecting X-rays produced by the first source of X-rays with a second linear X-ray detector after the X-rays have impinged upon and penetrated the object from a second angular orientation; moving the object between the first source of X-rays and the first and second linear X-ray detectors along a substantially linear path; producing a first X-ray shadowgraph image of the object with the X-rays detected by the first linear X-ray detector as the object traverses the substantially linear path between the first source of X-rays and the first linear X-ray detector; producing a second X-ray shadowgraph image of the object with the X-rays detected by the second linear X-ray detector as the object traverses the substantially linear path between the first source of X-rays and the second linear X-ray detector; and combining the first and second X-ray shadowgraph images of the object to form a cross sectional image of the object, wherein the Z-axis position of the cross sectional image is accurately determined by generation or measurement of Z-axis warp compensation parameters. In some configurations, the method further comprises the step of collimating the first source of X-rays with a first collimator configured to direct X-rays emitted by the first source of X-rays toward the first linear X-ray detector and to block X-rays travelling in other directions. Similarly, the method may further comprise the step of collimating the first source of X-rays with a second collimator configured to direct X-rays emitted by the first source of X-rays toward the second linear X-ray detector and to block X-rays travelling in other directions. In some configurations, the method further comprises the steps of: providing a second source of X-rays; and positioning the second source of X-rays laterally with respect to the first source of X-rays; detecting X-rays produced by the second source of X-rays with a third linear X-ray detector after the X-rays have impinged upon and penetrated the object from a third angular orientation; and detecting X-rays produced by the second source of X-rays with a fourth linear X-ray detector after the X-rays have impinged upon and penetrated the object from a fourth angular orientation. This method may further include the steps of: collimating the second source of X-rays with a third collimator configured to direct X-rays emitted by the second source of X-rays toward the third linear X-ray detector and to block X-rays travelling in other directions; and collimating the second source of X-rays with a fourth collimator configured to direct X-rays emitted by the second source of X-rays toward the fourth linear X-ray detector and to block X-rays travelling in other directions.

In a fourth embodiment, the invention is an imaging system comprising: a first X-ray source; a first linear X-ray detector positioned to intercept X-rays emitted by the first X-ray source at a first angle; a second linear X-ray detector positioned to intercept X-rays emitted by the first X-ray source at a second angle; a linear motion system to which the first X-ray source and the first and second linear X-ray detectors are mounted, the linear motion system further having a path for a stationary object under test to pass, the linear motion system configured to transport the first X-ray source and the first and second linear X-ray detectors past the stationary object under test such that the X-rays emitted at the first angle and the second angle and detected by the first linear X-ray detector and the second linear X-ray detector, respectively, after having passed through the stationary object under test, thereby form a first shadowgraph image and a second shadowgraph image of the stationary object under test; and a control system connected to the linear motion system, the first linear X-ray detector and the second linear X-ray detector, wherein the control system regulates the linear motion system and the formation of the first and second shadowgraph images to produce a laminographic cross sectional image of a cutting plane of the stationary object under test, wherein the position of the cutting plane is accurately determined by the control system by generation or measurement of Z-axis warp compensation parameters. In some configurations, a first collimator is positioned with respect to the first X-ray source such that the first collimator is configured to direct X-rays emitted by the first X-ray source toward the first linear X-ray detector and to block X-rays travelling in other directions. Similarly, a second collimator may be positioned with respect to the first X-ray source such that the second collimator is configured to direct X-rays emitted by the first X-ray source toward the second linear X-ray detector and to block X-rays travelling in other directions. In certain configurations, the imaging system further comprises: a second X-ray source positioned on the linear motion system laterally with respect to the first X-ray source; a third linear X-ray detector positioned on the linear motion system to intercept X-rays emitted by the second X-ray source at a third angle; and a fourth linear X-ray detector positioned on the linear motion system to intercept X-rays emitted by the second X-ray source at a fourth angle.

In a fifth embodiment, the invention includes a method of producing a cross sectional image of a stationary object comprising the steps of: providing a first source of X-rays; detecting X-rays produced by the first source of X-rays with a first linear X-ray detector after the X-rays have impinged upon and penetrated the stationary object from a first angular orientation; detecting X-rays produced by the first source of X-rays with a second linear X-ray detector after the X-rays have impinged upon and penetrated the stationary object from a second angular orientation; moving the first source of X-rays and the first and second linear X-ray detectors along a substantially linear path past the stationary object such that the X-rays from the first source of X-rays penetrate the stationary object and are detected by the first and second linear X-ray detectors; producing a first X-ray shadowgraph image of the stationary object with the X-rays detected by the first linear X-ray detector as the first linear X-ray detector and the first source of X-rays traverse the substantially linear path past the stationary object; producing a second X-ray shadowgraph image of the stationary object with the X-rays detected by the second linear X-ray detector as the second linear X-ray detector and the first source of X-rays traverse the substantially linear path past the stationary object; and combining the first and second X-ray shadowgraph images of the stationary object to form a cross sectional image of the stationary object, wherein the Z-axis position of the cross sectional image is accurately determined by generation or measurement of Z-axis warp compensation parameters. In some configurations, the method further comprises the steps of: collimating the first source of X-rays with a first collimator configured to direct X-rays emitted by the first source of X-rays toward the first linear X-ray detector and to block X-rays travelling in other directions; and collimating the first source of X-rays with a second collimator configured to direct X-rays emitted by the first source of X-rays toward the second linear X-ray detector and to block X-rays travelling in other directions. In some configurations, the method further comprises the steps of: providing a second source of X-rays; and positioning the second source of X-rays laterally with respect to the first source of X-rays. This method may further include the steps of: detecting X-rays produced by the second source of X-rays with a third linear X-ray detector after the X-rays have impinged upon and penetrated the stationary object from a third angular orientation; and detecting X-rays produced by the second source of X-rays with a fourth linear X-ray detector after the X-rays have impinged upon and penetrated the stationary object from a fourth angular orientation.

In a sixth embodiment, the invention includes an electrical connection inspection device comprising: a source of X-rays which emits X-rays through an electrical connection from a plurality of positions; an X-ray detector system positioned to receive the X-rays produced by the source of X-rays which have penetrated the electrical connection, the X-ray detector system further comprising an output which emits data signals corresponding to an X-ray image of the electrical connection produced by the X-rays received and detected by the X-ray detector system after penetrating the electrical connection; and an analysis system comprising: an image memory which stores the detector data signals thereby forming an image database which contains information sufficient to form a cross-sectional image of a cutting plane of the electrical connection; and an image processor which searches the image database for a specific pre-determined feature located at a first Z-axis level in the electrical connection and combines the detector data signals with reference to the first Z-axis level to form a specific Z-level image database which contains information sufficient to form a cross-sectional image of a cutting plane of the electrical connection at a second Z-axis level in the electrical connection. In some configurations, the source of X-rays comprises a plurality of X-ray sources and/or the X-ray detector system comprises a plurality of X-ray detectors. In certain configurations, the analysis system further comprises an image section which produces the cross-sectional image of a cutting plane of the electrical connection from the image database. In some configurations, the first Z-axis level and the second Z-axis level are the same.

In a seventh embodiment, the invention includes an inspection device comprising: a source of penetrating radiation which emits radiation through a test object from a plurality of positions; a detector system positioned to receive the radiation produced by the source of penetrating radiation which has penetrated the test object, the detector system further comprising an output which emits data signals corresponding to a penetrating radiation image of the test object produced by the radiation received and detected by the detector system after penetrating the test object; and an analysis system comprising: an image memory which stores the detector data signals thereby forming an image database which contains information sufficient to form a cross-sectional image of a cutting plane of the test object; and an image processor which searches the image database for a specific pre-determined feature located at a first Z-axis level in the test object and combines the detector data signals with reference to the first Z-axis level to form a specific Z-level image database which contains information sufficient to form a cross-sectional image of a cutting plane of the test object at a second Z-axis level in the test object. In some configurations, the source of penetrating radiation comprises a plurality of penetrating radiation sources and/or the detector system comprises a plurality of detector systems. In certain configurations, the analysis system further comprises an image section which produces the cross-sectional image of a cutting plane of the test object at a second Z-axis level in the test object from the Z-level image database.

In an eighth embodiment, the invention further includes a method for inspecting an electrical connection comprising the steps of: directing X-rays through the electrical connection from a plurality of positions; detecting X-rays transmitted through the electrical connection from the plurality of positions with an X-ray detector system having an output which emits data signals corresponding to an X-ray image of the electrical connection produced by X-rays received and detected by the X-ray detector system after penetrating the electrical connection; storing the X-ray detector data signals corresponding to the X-ray image of the electrical connection; creating a database of information from the X-ray detector data signals which contains information sufficient to form a cross-sectional image of a cutting plane of the electrical connection; searching the database of information for a specific pre-determined feature located at a first Z-axis level in the electrical connection; and combining the X-ray detector data signals with reference to the first Z-axis level to form a specific Z-level image database which contains information sufficient to form a cross-sectional image of a cutting plane of the electrical connection at a second Z-axis level in the electrical connection.

In a ninth embodiment, the invention includes an apparatus for producing cross-sectional images of an object at a first Z-level of the object with reference to a second Z-level of the object comprising: an imaging system for producing a first transmission shadowgraph image of the object from a first perspective and a second transmission shadowgraph image of the object from a second perspective, wherein the first transmission shadowgraph image includes an image of a specific pre-determined feature located at the second Z-level of the object and the second transmission shadowgraph image includes an image of the specific pre-determined feature located at the second Z-level of the object; and an image analysis system comprising: an image memory which stores the first and second transmission shadowgraph images; an image processor which searches the first and second transmission shadowgraph images for the images of the specific pre-determined feature located at the second Z-level of the object and combines the first and second transmission shadowgraph images with reference to the second Z-level of the object to form a cross-sectional image of the first Z-level of the object wherein the location of the first Z-level of the object is determined by reference to the location of the second Z-level of the object.

These and other characteristics of the present invention will become apparent through reference to the following detailed description of the preferred embodiments and accompanying drawings.

BRIEF DESCRIPTION OF THE DRAWINGS

FIGS. 6a–6d show conventional shadowgraph images of the test object shown in FIG. 5 formed in each of four linear X-ray detectors.

FIGS. 11a–11d show conventional shadowgraph images of a close-up of one of the leads of the test object shown in FIG. 10 formed in each of four linear X-ray detectors and the location of one of the pre-determined features selected to be used in the calculations for automatic warp compensation.

FIG. 12 is a flowchart illustrating the process for automatically calculating the warpage compensation.

DETAILED DESCRIPTION OF THE PREFERRED EMBODIMENTS

Figure 1:
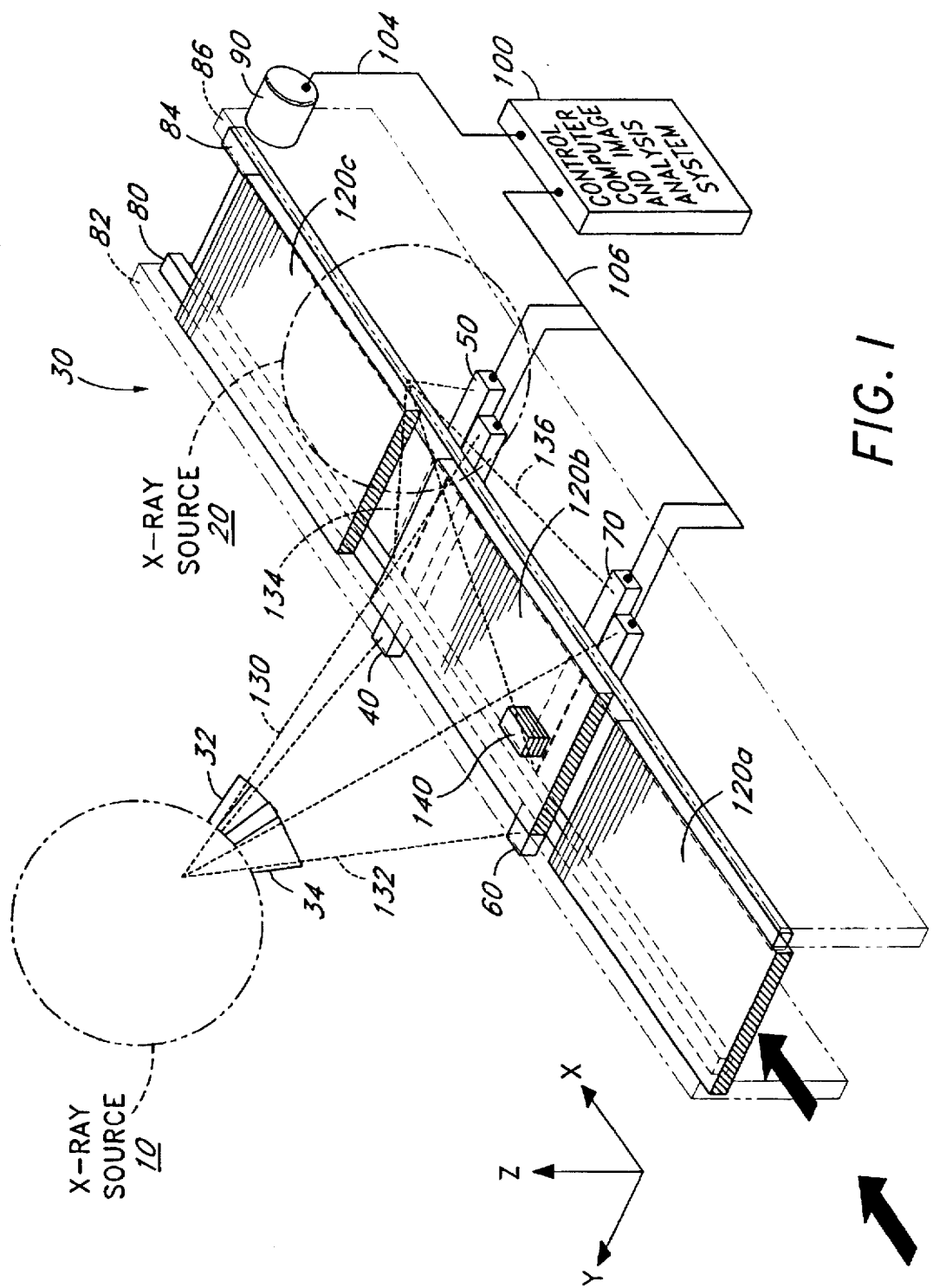
FIG. 1 shows a perspective view of a continuous linear scan laminography system in accordance with the present invention.

Shown in FIGS. 1, 2, 3 and 4 are a perspective view, a top view, a side view and an end view, respectively, of a continuous linear scan laminography system in accordance with the present invention. Referring to FIGS. 1, 2, 3 and 4, a first X-ray source 10 and a second X-ray source 20 are positioned above and along opposing sides of a conveyor system 30. The first X-ray source 10 includes a front collimator 32 and a rear collimator 34. Similarly, the second X-ray source 20 includes a front collimator 36 and a rear collimator 38. A first linear X-ray detector 40 is located adjacent to a second linear X-ray detector 50 to the right (positive X-direction) of a centerline (not shown) along the Y-direction defined by connecting the first X-ray source 10 with the second X-ray source 20. A third linear X-ray detector 60 is located adjacent to a fourth linear X-ray detector 70 to the left (negative X-direction) of the centerline connecting the first and second X-ray sources 10, 20. Each of the first, second, third and fourth linear X-ray detectors 40, 50, 60, 70 are located below the conveyor system 30. Conveyor system 30 further includes a first chain drive mechanism 80 and a first guide rail 82 on a first side and a second chain drive mechanism 84 and a second guide rail 86 on a second side. A synchronized drive motor 90 is connected to the first and second chain drive mechanisms 80, 84. The synchronized drive motor 90 is connected to a control computer and image analysis system 100 by motor power and control lines 104. The control computer and image analysis system 100 is also connected to the first, second, third and fourth linear X-ray detectors 40, 50, 60, 70 by means of detector power, control and signal lines 106.

Figure 2:
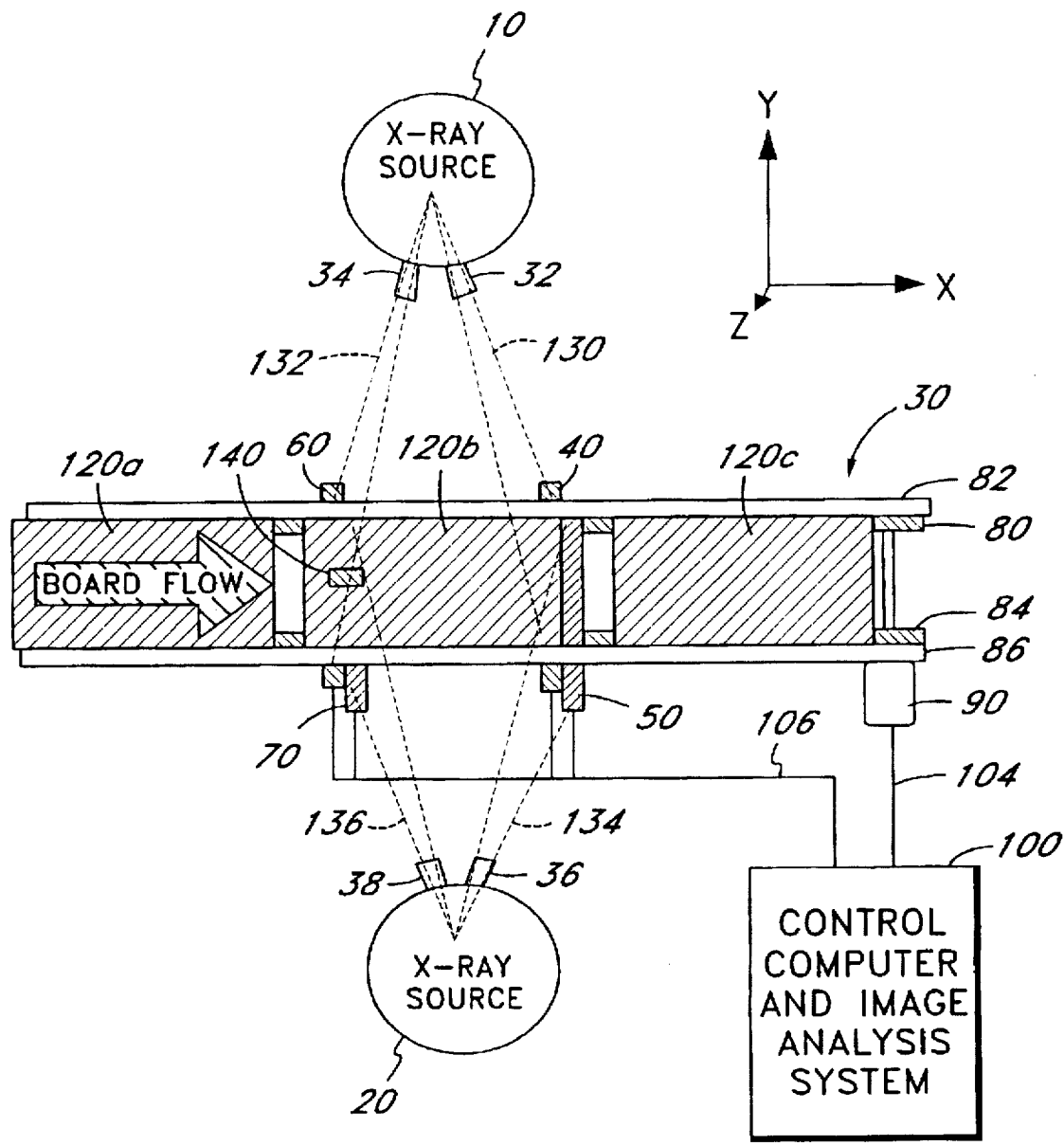
FIG. 2 shows a top view of the continuous linear scan laminography system of FIG. 1.
Figure 3:
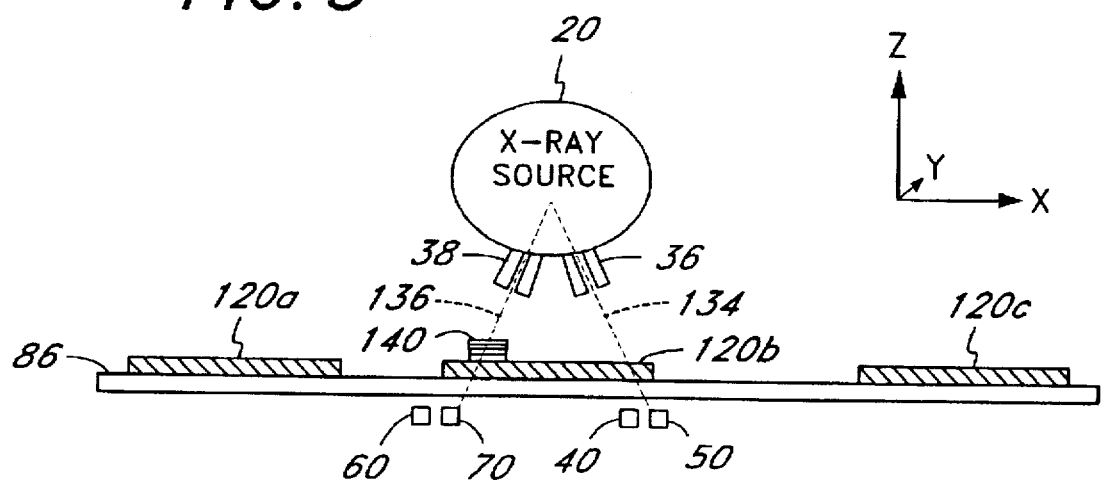
FIG. 3 shows a side view of the continuous linear scan laminography system shown in FIGS. 1 and 2.

In operation, circuit boards 120a, 120b, 120c are positioned onto the chain drive mechanisms 80, 84 and guided through the conveyor system 30 by the guide rails 82, 86. For purposes of describing the operation of the invention, the size of the circuit boards 120 is taken to be approximately 8.5 inches by 12 inches. Other sizes may also be used and these dimensions are in no way meant to be limiting. The circuit boards 120a, 120b, 120c are smoothly advanced by the chain drive mechanisms 80, 84 at a constant velocity of approximately 0.3 inches per second by the synchronized drive motor 90. The circuit boards 120a, 120b, 120c are separated from each other by approximately 0.7 inches. The synchronized drive motor 90 is operated by the control and image analysis computer 100 through the motor power and control lines 104. As shown in FIGS. 1 and 2: a) the inspection of circuit board 120c has been completed; b) the inspection of circuit board 120b is in progress; and c) circuit board 120a has just been loaded onto the conveyor system 30 and will be inspected immediately after the inspection of circuit board 120b is complete.

X-Ray Generation and Collimation

Figure 4:
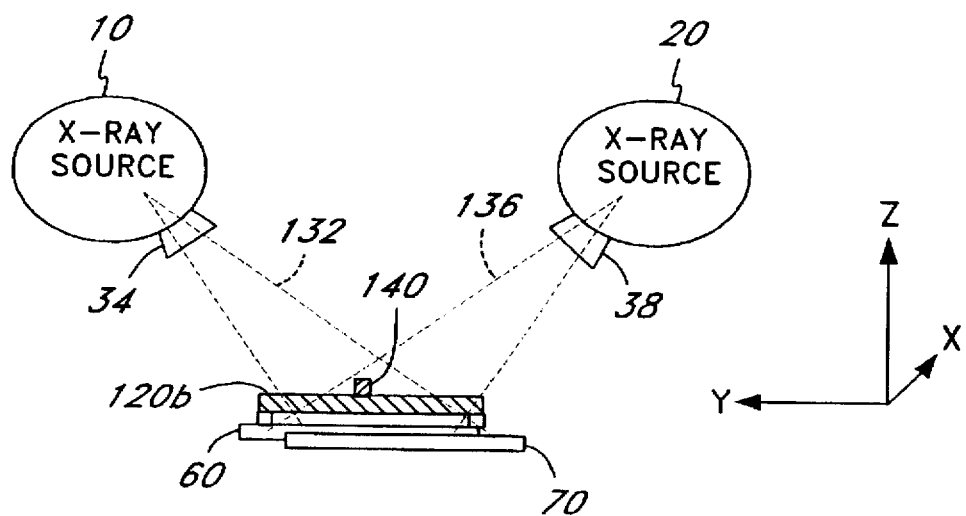
FIG. 4 shows an end view from the circuit board loading end of the continuous linear scan laminography system shown in FIGS. 1, 2 and 3.

The X-ray sources 10 and 20 are collimated by collimators 32, 34, 36, 38 to limit the angular spread of radiation emitted by the first and second X-ray sources 10, 20 in both the X-direction and the Y-direction so that each X-ray source 10, 20 produces two fan beams of X-rays. The first X-ray source 10 gives off fan beams of X-rays 130, 132 while the second X-ray source 20 gives off fan beams of X-rays 134, 136. The X-ray sources 10, 20 are mounted in a conventional manner at a location which provides appropriate laminographic angles for production of cross sectional images of the circuit board 120b. For example, as can be seen in FIGS. 1 and 4, the X-ray sources 10, 20 are located at angles of approximately ±45 degrees with respect to the normal to the circuit board 120b (Z-direction). Additionally, the X-ray sources 10, 20 are located a distance from the circuit board 120b and linear X-ray detectors 40, 50, 60, 70 such that the combination of: 1) the focal spot sizes of the X-ray sources 10, 20; 2) the standoff distance between the circuit board 120b and the linear X-ray detectors 40, 50, 60, 70 (typically one inch or less); and 3) the power output of the X-ray sources 10, 20; all cooperate to provide sufficient light levels at the linear X-ray detectors 40, 50, 60, 70 to produce high resolution images.

The preferred X-ray sources 10, 20 are standard industrial X-ray tubes operable at voltages up to 125 kilovolts with an anode current ranging from approximately 0.1 ma to 1.0 ma. The first and second X-ray tubes 10, 20 may both be powered by a single high voltage (HV) power supply (not shown). The preferred focal spot size of the X-ray tubes 10, 20 is in the range of from 100 microns to 1000 microns in diameter.

The circuit board 120b being inspected is irradiated by X-rays generated by X-ray sources 10, 20. The angular spread of the X-rays emitted from the first X-ray source 10 are: 1) collimated in the X-direction by the front collimator 32 into the narrow fan beam of X-rays 130 configured to illuminate only a first small portion of the circuit board 120b and the front surface of the first linear X-ray detector 40 after having passed through the first small portion of the circuit board 120b illuminated; and 2) collimated in the X-direction by the rear collimator 34 into the narrow fan beam of X-rays 132 configured to illuminate only a third small portion of circuit board 120b and the front surface of the third linear X-ray detector 60 after having passed through the third small portion of circuit board 120b. Similarly, X-rays emitted from the second X-ray source 20 are: 1) collimated in the X-direction by the front collimator 36 into the narrow fan beam of X-rays 134 configured to illuminate only a second small portion of the circuit board 120b and the front surface of the second linear X-ray detector 50 after having passed through the second small portion of circuit board 120b; and 2) collimated in the X-direction by the rear collimator 38 into the narrow fan beam of X-rays 136 configured to illuminate only a fourth small portion of the circuit board 120b and the front surface of the fourth linear X-ray detector 70 after having passed through the fourth small portion of the circuit board 120b. Thus, the first linear X-ray detector 40 receives only X-rays generated by the first X-ray source 10 and emitted through the front collimator 32; the second linear X-ray detector 50 receives only X-rays generated by the second X-ray source 20 and emitted through the front collimator 36; the third linear X-ray detector 60 receives only X-rays generated by the first X-ray source 10 and emitted through the rear collimator 34; and the fourth linear X-ray detector 70 receives only X-rays generated by the second X-ray source 20 and emitted through the rear collimator 38. Additionally, as best illustrated in FIGS. 2 and 4, each of the narrow fan beams of X-rays 130, 132, 134, 136 is collimated in the Y-direction by its respective collimator 32, 34, 36, 38 in a manner which prevents X-rays from extending beyond the horizontal extent (Y-direction) of its respective linear X-ray detector 40, 50, 60, 70.

X-Ray Detection, Image Formation and Data Handling

The conveyor system 30 transports the circuit board under test 120b through the four collimated fan beams of X-rays 130, 132, 134, 136. X-rays which pass through the circuit board 120b are detected by the linear X-ray detectors 40, 50, 60, 70. Each linear X-ray detector 40, 50, 60, 70 converts the pattern of X-rays that have passed through the circuit board under test 120b into an electrical signal that is sent over the detector power, control, and signal lines 106 to the control computer and image analysis system 100 for processing.

The linear X-ray detectors 40, 50, 60, 70 in the preferred embodiment are approximately 8.5 inches wide and have a horizontal resolution (X-direction) of approximately 16–20 line pair/millimeter (lp/mm) resolution. This corresponds to 400 to 500 line pair/inch or 800 to 1000 dots per inch in the terminology of desk top scanning. Each of the linear X-ray detectors 40, 50, 60, 70 has built in digitizing electronics for providing a digitized data stream of 8 to 16 bits which interfaces directly to the control computer and image analysis system 100. The linear X-ray detectors 40, 50, 60, 70 are formed from standard line scan detectors used in desk top publishing scanners. Each linear X-ray detector 40, 50, 60, 70 has a thin coating of X-ray sensitive phosphor deposited directly on the front of the detector's light sensitive area. Typically, the X-ray sensitive phosphor is gadolinium oxysulfide, however, other materials may also be used, for example, cadmium tungstate. The data from each linear X-ray detector 40, 50, 60, 70 generates a complete X-ray shadowgraph picture of the 8.5" by 12" circuit board under test 120b as it passes over the respective detector. (See FIGS. 6a–6d)

The linear X-ray detectors 40, 50, 60, 70 are similar to charge coupled devices (CCD) commonly found in video cameras. The charge coupled devices used in video cameras are typically solid state integrated circuit chips having a two dimensional array of discrete light sensitive elements formed thereon. The linear X-ray detectors 40, 50, 60, 70 are linear or one dimensional arrays of discrete light sensitive elements formed on a single chip. Linear arrays are commonly used in baggage scanners at airport security stations to produce low resolution X-ray shadowgraph images of baggage.

One suitable linear X-ray detector, known as the Radiographic Line Scan (RLS) detector, is available commercially from Bio-Imaging Research, Inc. in Lincolnshire, Ill. A paper by Charles R. Smith and Joseph W. Erker, entitled; "Low cost, high resolution x-ray detector system for digital radiography and computed tomography"; *SPIE X-Ray Detector Physics and Applications II*, Vol. 2009, 1993, pp. 31–35, includes a detailed description of this device. Another suitable linear detector, known as the IL-C8-6000 Turbosensor, is available from Dalsa in Waterloo, Canada. Another producer of linear arrays is EG&G Reticon which produces a diode array, model number RL2048S, which is a monolithic self-scanning linear photodiode array with 2048 photodiode sensor elements with 25 micron center-to-center spacing. This device consists of a row of photodiodes, each with an associated storage capacitor on which to integrate photo current and a multiplex switch for readout by an independent integrated shift register. Thus, there several sources of commercially available linear array devices which can be adapted for use in the present invention.

While it is preferred that each of the 8.5" long linear X-ray detectors 40, 50, 60, 70 be a single unit, one skilled in the art will recognize that shorter units may be combined to achieve any desired overall length. That is, two of the above mentioned IL-CS-6000 Turbosensors, each of which is 6" long, may be mounted slightly staggered so that the end of one matches up to the end of the other, thus providing coverage for a 12 inch wide circuit board. Alternatively, a lens system or fiber optic reducer may be positioned between an X-ray scintillation screen of the desired length and the linear sensor of a shorter length. The image produced on the screen is then focused by the lens system onto the linear sensor having a shorter length or directed by appropriate reducing fiber optics onto the linear sensor.

The data from the linear X-ray detectors 40, 50, 60, 70 is stored in a memory bank within the control computer and image analysis system 100. For a system having a resolution of 800 DPI and an 8.5 inch width, there are 6800 pixels along the 8.5 inch width (Y-direction), corresponding to the width of the circuit board under test 120b. At 800 DPI resolution, the 12 inch length of the circuit board under test 120b corresponds to 9600 pixels along the length direction (X-direction). Thus, the memory bank used to store the complete image of the 8.5" by 12" circuit board 120b needs to have a storage capacity of 6800×9600×8 bits or approximately 65 megabytes. Since there are 4 linear X-ray detectors 40, 50, 60, 70, a total of 260 megabytes of memory is required. Additionally, if the system is to analyze the images for one circuit board 120c while the system acquires the images of the next circuit board 120b, the memory bank within the control computer and image analysis system 100 must be doubled for a total of 520 megabytes. The memory bank is designed in such a way that a first half of the memory bank is connected to the linear X-ray detectors 40, 50, 60, 70 while an image is being acquired while a second half of the memory bank, which contains the images for the previous circuit board, is connected to the image analysis portion of the control computer and image analysis system 100. When the image acquisition into the first half of the memory bank and the image analysis of the data in the second half of the memory bank are complete, the first half of the memory bank is disconnected from the linear X-ray detectors 40, 50, 60, 70 and connected to the image analysis portion of the control computer and image analysis system 100. Likewise, the second half of the memory bank is disconnected from the image analysis portion of the control computer and image analysis system 100 and connected to the linear X-ray detectors 40, 50, 60, 70.

Laminographic Cross Sectional Image Formation

As previously described, each of the first, second, third and fourth linear X-ray detectors 40, 50, 60, 70 produces a conventional X-ray shadowgraph image of the object being inspected, for example, a circuit board 120b. A laminographic cross sectional image of the object is formed from the four resulting shadowgraph images in a conventional manner. This technique is discussed in detail in U.S. Pat. No. 3,818,220 entitled "VARIABLE DEPTH LAMINAGRAPHY", issued to Richards and U.S. Pat. No. 3,499,146 entitled "VARIABLE DEPTH LAMINAGRAPHY WITH MEANS FOR HIGHLIGHTING THE DETAIL OF SELECTED LAMINA", issued to Richards.

Figure 5:
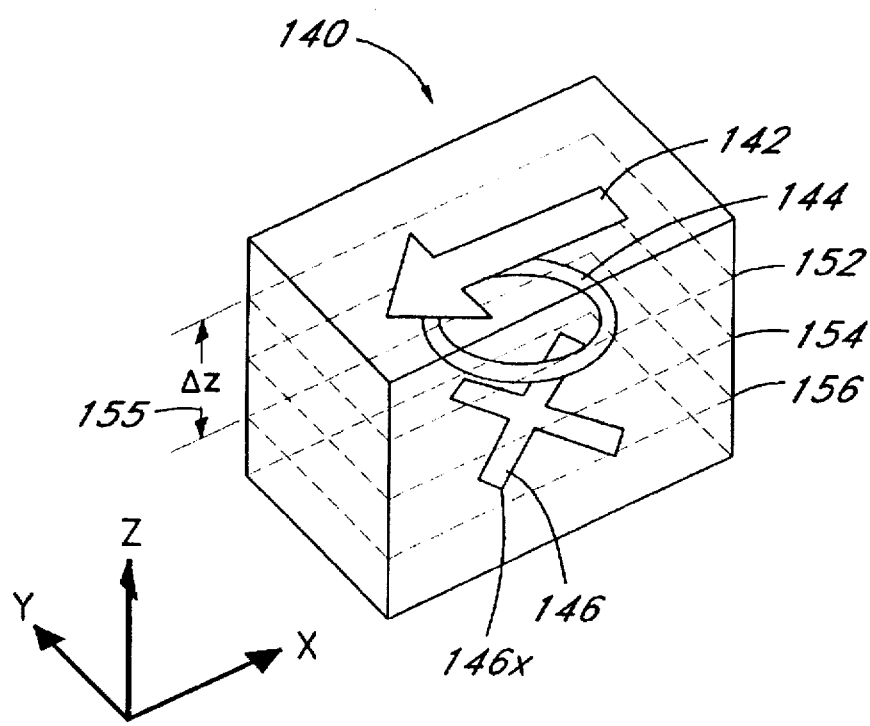
FIG. 5 shows a test object for demonstrating laminography.

FIG. 5 shows a test object 140 for illustrating the technique of creating a laminographic cross sectional image of a selected plane within the test object 140 from four shadowgraph images 160, 260, 360, 460 (see FIGS. 6a–6d). The test object 140 contains patterns in the shape of an arrow 142, a circle 144 and a cross 146 embedded within the test object 140 in three different planes 152, 154 and 156, respectively.

Shown in FIGS. 6a–6d are the shadowgraph images created by the four linear X-ray detectors 40, 50, 60, 70. The test object 140 is oriented on the conveyor system 30 as shown in FIGS. 1–4 with the arrow 142 pointing in the negative X-direction, i.e., toward the circuit board 120a. FIG. 6b shows a shadowgraph image 160 of the test object 140 created by the first linear X-ray detector 40. The arrow 142 forms an image 162a, the circle 144 forms an image 162c and the cross 146 forms an image 162x. FIG. 6a shows a shadowgraph image 260 of the test object 140 created by the second linear X-ray detector 50. The arrow 142 forms an image 262a, the circle 144 forms an image 262c and the cross 146 forms an image 262x. FIG. 6d shows a shadowgraph image 360 of the test object 140 created by the third linear X-ray detector 60. The arrow 142 forms an image 362a, the circle 144 forms an image 362c and the cross 146 forms an image 362x. FIG. 6c shows a shadowgraph image 460 of the test object 140 created by the fourth linear X-ray detector 70. The arrow 142 forms an image 462a, the circle 144 forms an image 462c and the cross 146 forms an image 462x.

Figure 7:
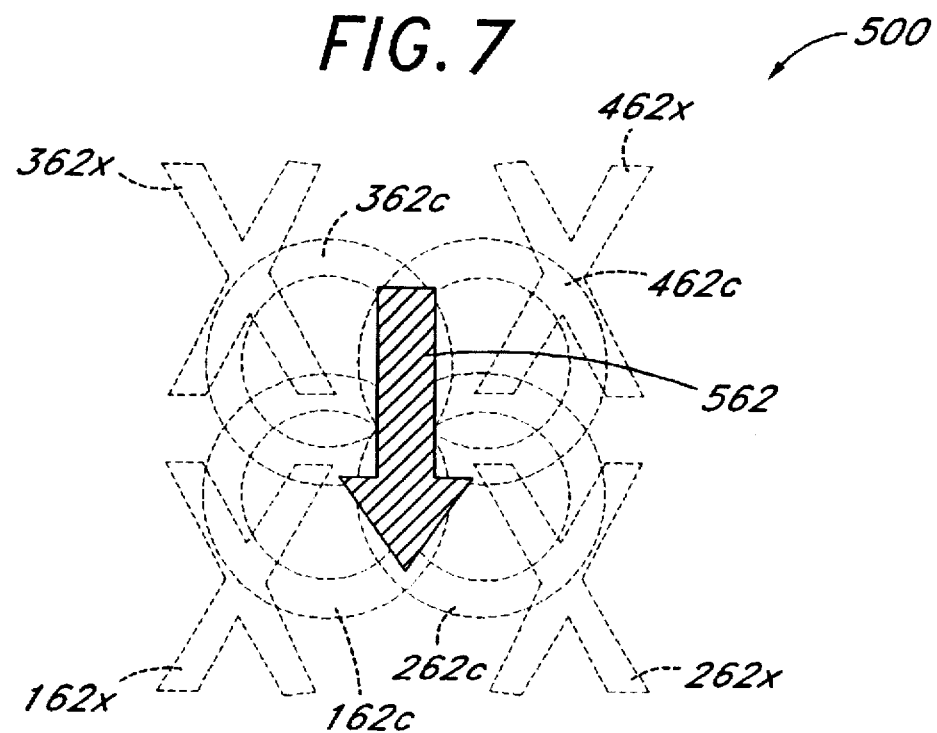
FIG. 7 shows a cross sectional laminographic image of the test object at one focal plane derived from the combination of the conventional shadowgraph images shown in FIGS. 6a–6d.

The formation of a laminographic cross sectional image of a selected plane within the test object 140 from the four shadowgraph images 160, 260, 360, 460 is accomplished by adding the four shadowgraph images 160, 260, 360, 460 together in a way which reinforces the images in selected plane at the sacrifice of the images in the other planes. The manner in which the four shadowgraph images 160, 260, 360, 460 are added together to form a laminographic cross sectional image 500 of the arrow 142 in the plane 152 is shown in FIG. 7. As illustrated in FIG. 7, each of the four shadowgraph images 160, 260, 360, 460 is shifted by a distance appropriate for each respective image in the X-direction and/or the Y-direction by a distance which causes the four images of the arrow 162a, 262a, 362a, 462a to substantially overlap one another thereby forming a reinforced image of the arrow 562 in the laminographic cross sectional image 500. The area surrounding the reinforced image of the arrow 562 is comprised of the four images of the circle 162c, 262c, 362c, 462c and the four images of the cross 162x, 262x, 362x, 462x. Since the images of the circle and the cross are scattered about at different locations, they do not reinforce each other as do the overlapping images of the arrow 162a, 262a, 362a, 462a. In a similar manner, the four shadowgraph images 160, 260, 360, 460 may be added together to form laminographic cross sectional images of the circle 144 in the plane 154 or the cross 146 in the plane 156 or any other preselected plane within the test object 140.

Figure 8:
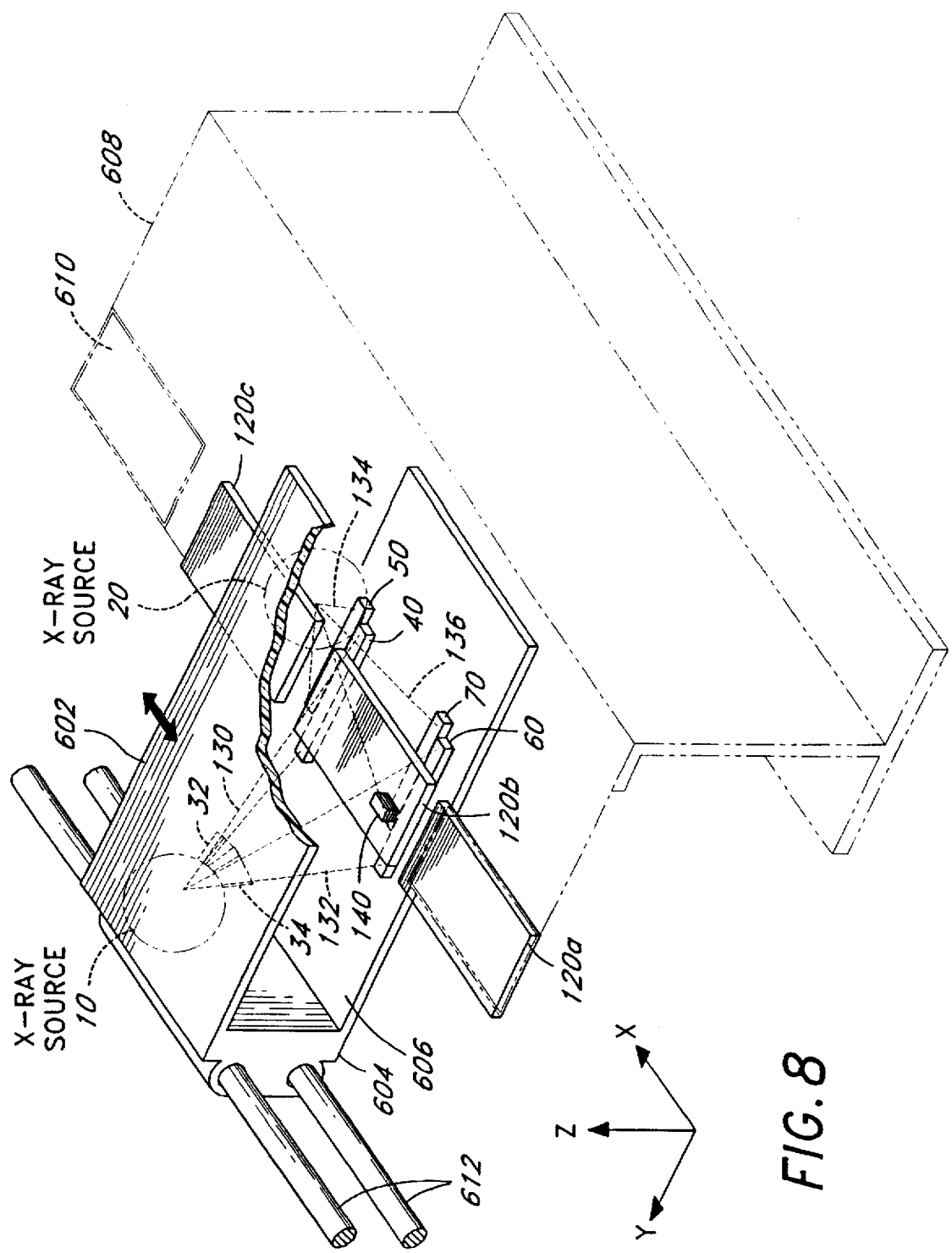
FIG. 8 shows a perspective view of an alternate embodiment of a continuous linear scan laminography system in accordance with the present invention.

The above described preferred embodiment describes a continuous scan apparatus and method for high speed, high resolution inspection which does not require motion of the detector, the X-ray tube, the spot of X-rays, or the beam of X-rays. The only motion required is a smooth linear motion of the test object to be imaged. However, one skilled in the art will recognize that an equivalent system is one in which the test object to be imaged remains stationary and the X-ray detector(s), the X-ray tube(s) and the beam(s) of X-rays execute a smooth linear motion with respect to the stationary test object to be imaged, thereby generating shadowgraph images which may be added together to form laminographic cross sectional images of any preselected plane within the stationary test object as previously described. FIG. 8 shows an example of such an equivalent system wherein the test object to be imaged remains stationary and the X-ray tube(s) and X-ray detector(s) execute a smooth linear motion with respect to the stationary test object to be imaged. In FIG. 8, the same reference numerals are used for identical or corresponding elements of the embodiments shown in previous figures.

As shown in FIG. 8, the first X-ray source 10 and the second X-ray source 20 are mounted on an upper arm 602 of a C-shaped channel support unit 604 such that they are positioned above and along opposing sides of the circuit boards 120 which are arranged on a circuit board support unit 608. The circuit board support unit 608 has apertures 610 over which the circuit boards 120 are arranged so that the X-ray beams 130, 132, 134, 136 pass through the circuit boards 120 only, i.e., not through the circuit board support unit 608, in their paths from the X-ray sources 10, 20 to the X-ray detectors 40, 50, 60, 70. The first X-ray source 10 includes the front collimator 32 and the rear collimator 34. Similarly, the second X-ray source 20 includes the front collimator 36 and the rear collimator 38 (not shown in FIG. 8). The first, second, third and fourth linear X-ray detectors 40, 50, 60, 70 are mounted on a lower arm 606 of the C-shaped channel support unit 604. The first linear X-ray detector 40 is positioned adjacent to the second linear X-ray detector 50 to the right (positive X-direction) of a centerline (not shown) along the Y-direction defined by connecting the first X-ray source 10 with the second X-ray source 20. The third linear X-ray detector 60 is located adjacent to the fourth linear X-ray detector 70 to the left (negative X-direction) of the centerline connecting the first and second X-ray sources 10, 20. Each of the first, second, third and fourth linear X-ray detectors 40, 50, 60, 70 are thus located below the circuit boards 120; the circuit board support unit apertures 610; and the circuit board support unit lower arm 606. The C-shaped channel support unit 604 is mounted on slide rails 612 thereby allowing the C-shaped channel support unit 604, along with the attached first and second X-ray sources 10, 20 and the first, second, third and fourth linear X-ray detectors 40, 50, 60, 70, to move as a unit in the positive and negative X-directions. The synchronized drive motor 90 (FIG. 1) controls the motion of the C-shaped channel support unit 604 on the slide rails 612. As previously discussed, the synchronized drive motor 90 is connected to the control computer and image analysis system 100 (FIG. 1). The control computer and image analysis system 100 is also connected to the first, second, third and fourth linear X-ray detectors 40, 50, 60, 70.

In operation, the embodiment of FIG. 8 works in same way as the FIG. 1 embodiment previously described with the following exception. In the FIG. 1 embodiment, a linear scan of the circuit boards is performed by holding the first and second X-ray sources 10, 20 and the first, second, third and fourth linear X-ray detectors 40, 50, 60, 70 in a fixed or stationary position and moving the circuit boards 120a, 120b, 120c through the X-ray beams 130, 132, 134, 136 on the conveyor system 30. In the FIG. 8 embodiment, a linear scan of the circuit boards by the X-ray beams 130, 132, 134, 136 is performed by holding the circuit boards 120a, 120b, 120c in a fixed or stationary position on the circuit board support unit 608 and moving the C-shaped channel support unit 604 with the attached first and second X-ray sources 10, 20 and the first, second, third and fourth linear X-ray detectors 40, 50, 60, 70 past the circuit boards 120 via the slide rails 612. One skilled in the art will recognize that the linear scans thus produced by the embodiments of FIG. 1 and FIG. 8 are equivalent.

Automatic Warp Compensation

The procedure for generating cross-sectional images was previously explained with reference to FIGS. 5, 6 and 7 for a test object 140. In summary, as illustrated in FIG. 7, each of the four shadowgraph images 160, 260, 360, 460 is shifted by a distance appropriate for each respective image in the X-direction and/or the Y-direction by a distance which causes the four images of the arrow 162a, 262a, 362a, 462a to substantially overlap one another thereby forming a reinforced image of the arrow 562 in the laminographic cross sectional image 500. The appropriate distances for shifting each of the four shadowgraph images 160, 260, 360, 460 is determined by the control computer and image analysis system 100 in the following manner. The computer 100 has access to the following data: a) CAD data for the test object 140 which includes a complete digital representation of the structure of the test object 140; and b) a digital representation of the continuous linear scan laminography system in accordance with the present invention which includes, for example, the locations and dimensions in the XYZ coordinate system of the first and second X-ray sources 10, 20; the first, second, third and fourth linear X-ray detectors 40, 50, 60, 70; and the conveyor system 30. Once loaded with this data, the control computer and image analysis system 100, using simple geometric ray projections, calculates theoretical images for each detector 40, 50, 60, 70, which correspond to the images shown in FIGS. 6a, 6b, 6c and 6d. For example, a ray projected from the second X-ray source 20 through the tip of the arrow 142 in the test object 140, terminates on the second linear X-ray detector 50 at an X-axis pixel location of 22 and a Y-axis pixel location of 44 as shown on FIG. 6a. (Note that in this example, the direction for scanning the data from the second linear X-ray detector 50 has been selected to be in the same direction as the positive Y-axis.) Similarly, the entire image 260 of the test object 140 shown in FIG. 6a is calculated by the computer using ray projections. In the ideal situation where the hardware, i.e., the continuous linear scan laminography system, is exactly the same as its digital representation and the test object is exactly as described in the CAD files, the actual images formed by the linear X-ray detectors 40, 50, 60, 70 and the theoretical images calculated by the computer 100 will be identical.

In an imaging operation mode, the computer system uses the CAD data for the test object 140 and the digital representation of the continuous linear scan laminography system to calculate the appropriate pixel shifts required for combining the four images (FIGS. 6a, 6b, 6c and 6d) to produce a laminographic image of a specific Z-axis plane of the test object 140. For example, the laminographic image of the Z-axis plane which includes the arrow 142 (see FIG. 7) can be generated by the following pixel shifts of FIGS. 6b, 6c and 6d with respect to FIG. 6a. a) FIG. 6a—no shift; b) FIG. 6b: X-shift=22−22=0; Y-shift=44−18=26; c) FIG. 6c: X-shift=22−7=15; Y-shift=44−39=5; and d) FIG. 6d: X-shift=22−6=16; Y-shift=44−18=26. Thus, in operation, the four images (FIGS. 6a, 6b, 6c and 6d) are acquired by the linear X-ray detectors 40, 50, 60, 70 and received by the computer 100 which then uses the above calculated pixel shifts to combine the four images to produce the desired laminographic image of the Z-axis plane which includes the arrow 142 (see FIG. 7).

This process works fine as long as the CAD data for the test object 140 accurately describes the actual object 140. However, if the actual test object 140 is warped, i.e., distorted in the Z-axis so that the actual Z-axis distance of the plane 152 of test object 140 which contains the arrow 142 is different than that contained in the CAD data, then the CAD data is not accurate and the computer will generate a different laminographic image than that desired. That is, when the computer uses the above described pixel shifts for FIGS. 6b, 6c and 6d with respect to FIG. 6a to generate a laminographic image of the Z-axis plane which includes the arrow 142, it will actually produce a laminographic image of a different Z-axis plane which is either above or below the plane 152 of the test object 140, depending upon the direction in which the test object 140 is warped. Thus, the following Z-axis warp compensation mode of operation describes a process whereby the computer determines or measures the actual Z-axis location of a specific plane in the test object 140 by analyzing the four images 160, 260, 360 and 460. Once the computer has determined or measured the actual location of one specific Z-axis plane in the test object, other Z-axis planes may be located by reference thereto.

In the Z-axis warp compensation mode of operation, the computer searches each of the shadowgraph images 160, 260, 360 and 460 for a specific pre-determined feature to use as a fiducial mark, for example, the tip of the arrow 142, the center of the circle 144, a specific edge of the cross 146, etc. The actual location of the selected specific pre-determined feature along the X-axis and the Y-axis is measured in each shadowgraph image 160, 260, 360 and 460 and compared to the theoretical location (i.e., CAD data determined location) of the selected specific pre-determined feature for each image to determine the relative position of the actual Z-axis location of the specific plane in the test object 140 with respect to the theoretical Z-axis location of the specific plane in the test object 140. Thus, the difference between the actual Z-axis location and the theoretical Z-axis location is a measure of the amount of warpage of the test object 140 along the Z-axis.

A map of the Z-axis warpage of the test object, i.e., a display of the warp factors distributed over the surface of the test object, is easily generated by using multiple specific pre-determined features which are also distributed throughout the test object at different locations.

Production of a cross-sectional image of a specific Z-axis plane within the test object, corrected for Z-axis warpage, is also accomplished using this technique. For example, if a cross-sectional image of a plane in the test object which is 1 mm above the plane containing the arrow, the above described process is used to identify the plane containing the arrow and calculate the pixel shifts required to produce an image of the plane containing the arrow. Then, the measured position of the arrow and the known geometrical parameters for the test object and the continuous linear scan laminography system are used by the computer to calculate the pixel shifts required to produce an image of any Z-level in the test object relative to the actual, i.e., measured, plane of the arrow. In this example, the pixel shifts required to produce a cross-sectional image of the plane in the test object which is 1 mm above the plane containing the arrow are calculated and used to produce the desired image.

For example, the pixel shifts for producing a cross-sectional image of a new Z-level ($Z_{New}$) with reference to the Z-level containing the predetermined feature ($Z_{PF}$) are determined or calculated by the computer in the following manner. Using the test object 140 (FIG. 5) by way of example, the pixel shifts for producing a cross-sectional image of the Z-level 152 containing the arrow 142 are determined by searching the four shadowgraph images 160, 260, 360, 460 (FIGS. 6a–6d) for the location of the tip of the arrow, i.e., the predetermined feature. The search of shadowgraph images 160, 260, 360, 460 empirically determines that: a) the tip of the arrow image is located at X-axis pixel location 22 and Y-axis pixel location 44 in shadowgraph image 260 (FIG. 6a); b) the tip of the arrow image is located at X-axis pixel location 22 and Y-axis pixel location 18 in shadowgraph image 160 (FIG. 6b); c) the tip of the arrow image is located at X-axis pixel location 7 and Y-axis pixel location 39 in shadowgraph image 460 (FIG. 6c); and d) the tip of the arrow image is located at X-axis pixel location 6 and Y-axis pixel location 18 in shadowgraph image 360 (FIG. 6d). It is important to note that these X-axis and Y-axis pixel locations are empirically determined, i.e., measured from the data (images) acquired by the computer. The pixel shifts for producing a laminographic image 500 (FIG. 7) of Z-level 152 containing the arrow 142 are simply the differences between these locations of the tip of the arrow image in shadowgraph images 160, 360, 460 with respect to the fourth image 260. The laminographic image 500 of Z-level 152 is produced by combining shadowgraph images 160, 260, 360, 460 with the following pixel shifts of FIGS. 6b, 6c and 6d with respect to FIG. 6a: a) FIG. 6a—no shift; b) FIG. 6b: X-shift=22−22=0; Y-shift=44−18=26; c) FIG. 6c: X-shift=22−7=15; Y-shift=44−39=5; and d) FIG. 6d: X-shift=22−6=16; Y-shift=44−18=26. In this manner, the present invention produces a laminographic image of a specific plane containing a predetermined feature by reference to the shadowgraph images of the predetermined feature. Thus, even if the test object is warped, the laminographic image is of that particular plane since it is referenced to the measured data and not the CAD data. Once a specific plane containing a predetermined feature has been identified, accurate laminographic images of other planes are produced by referencing them to the plane containing the predetermined feature, as shown by the following example.

This example discusses the process for producing a laminographic image of the plane 156 (FIG. 5) which is located a distance ΔZ 155 from the plane 152 containing the predetermined feature. The laminographic image of the plane 156 is produced by reference to the plane 152 containing the predetermined feature in following manner. After the computer has produced the laminographic image of the plane 152 containing the predetermined feature as described above, the following data is available to the computer: 1) the pixel shift values for producing a cross-sectional image of level 152; 2) the known locations of the X-ray sources 10, 20; and 3) the known locations of the detectors 40, 50, 60, 70. Given the additional information that the distance ΔZ 155 separates Z-level 152 and the new Z-level ($Z_{New}$) 156 at which a cross-section image is desired, the computer calculates the pixel shift values for generating a cross-sectional image of the new level ($Z_{New}$) 156. The computer performs this task by projecting a ray from each of the X-ray sources 10, 20 to their respective detectors 40, 50, 60, 70 through an arbitrarily chosen point in the new Z-level ($Z_{New}$) plane 156 thereby determining the pixel locations of the images formed by the arbitrarily chosen point on the images produced by detectors 40, 50, 60, 70. The pixel locations of the images formed by the arbitrarily chosen point in Z-level 156 are then measured relative to the empirically determined pixel locations of the images of the predetermined feature in Z-level 152. That is, all pixel locations are now referenced to the empirically determined pixel locations of the images of the predetermined feature. By way of example and for the purpose of clarifying the explanation, assume that the arbitrary point in Z-level 156 coincides with a corner 146x of the cross 146. Corner 146x produces images 246a, 146a, 446a, 346a on detectors 50, 40, 70, 60, respectively. Using the known locations of the X-ray sources 10, 20 and the known locations of the detectors 40, 50, 60, 70, the computer calculates that: a) a ray projected from X-ray source 20 to detector 50 through the arbitrary point (corner 146x) in the new Z-level ($Z_{New}$) 156 terminates on detector 50 forming the image 246a of corner 146x (FIG. 6a). As shown in FIG. 6a, the location of the image 246a is then measured to be 14 pixels in the negative X-direction from the X pixel location (22) of the image of the tip of the arrow, i.e., at an X pixel location of 8. Similarly, the location of the image 246a is measured to be 27 pixels in the negative Y-direction from the Y pixel location (44) of the image of the tip of the arrow, i.e., at a Y pixel location of 17. In a like manner, the pixel locations of the images 146a, 446a and 346a are measured (relative to the images of the tip of the arrow) to be at X,Y pixel locations of (8,30), (28,15) and (26,28), respectively. A laminographic image (not shown) of Z-level 156 is then produced by combining shadowgraph images 160, 260, 360, 460 with the following pixel shifts of FIGS. 6b, 6c and 6d with respect to FIG. 6a: a) FIG. 6a—no shift; b) FIG. 6b: X-shift=8−8=0; Y-shift=17−30=−13; c) FIG. 6c: X-shift=8−28=−20; Y-shift=17−15=2; and d) FIG. 6d: X-shift=8−26=−18; Y-shift=17−28=−11. In this manner, the present invention produces a laminographic image of a second specific plane 156 which is separated by a predetermined distance ΔZ 155 from a first specific plane 152 containing a predetermined feature (arrow tip) by reference to the shadowgraph images 160, 260, 360 460 of the predetermined feature. Thus, even if the test object is warped, the laminographic image of the second specific plane is truly the image of the plane which is separated from the first specific plane by the predetermined distance since it is referenced to the measured data from the first specific plane and not the CAD data.

Clearly, many variations of this technique are possible, depending upon the desired output. For example, compensation for board skew as the board flows through the present invention of a continuous linear scanning laminography system, creation of a warpage map of the test object, etc.

Production of a Z-axis warp map and production of a cross-sectional image of a specific Z-axis plane within the test object, corrected for Z-axis warpage are only two examples of how the technique of the present invention may be used. Numerous other applications, which will be appreciated by one skilled in the art, may also be implemented using the apparatus and method of the present invention. One specific application, the inspection of solder connections on printed circuit boards is described below.

Figure 9:
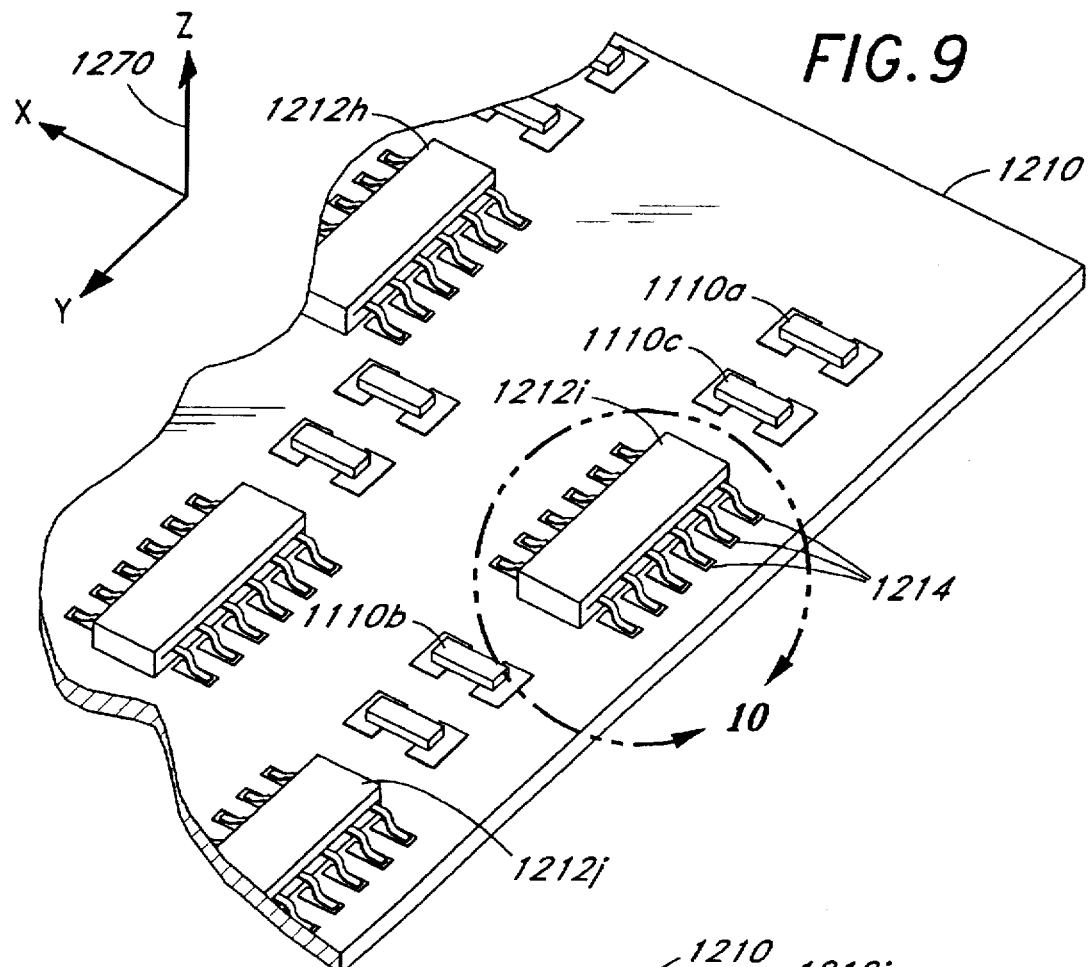
FIG. 9 shows a typical test object comprised of a circuit board upon which are located multiple electronic devices interconnected by multiple solder connections.

Shown in FIG. 9 is a typical test object comprised of a circuit board 1210 upon which are located multiple electronic devices 1212 and 1110 interconnected by multiple electrical connections 1214. In order to simplify the explanation of the automated analysis procedure for warp compensation, a specific type of electronic device and corresponding solder connection is singled out for detailed discussion. However, it will be understood that the invention is not to be limited by the specific device chosen and that the invention applies to numerous other types of devices, technologies, electrical connections, and even test objects that are other than circuit board assemblies.

Figure 10:
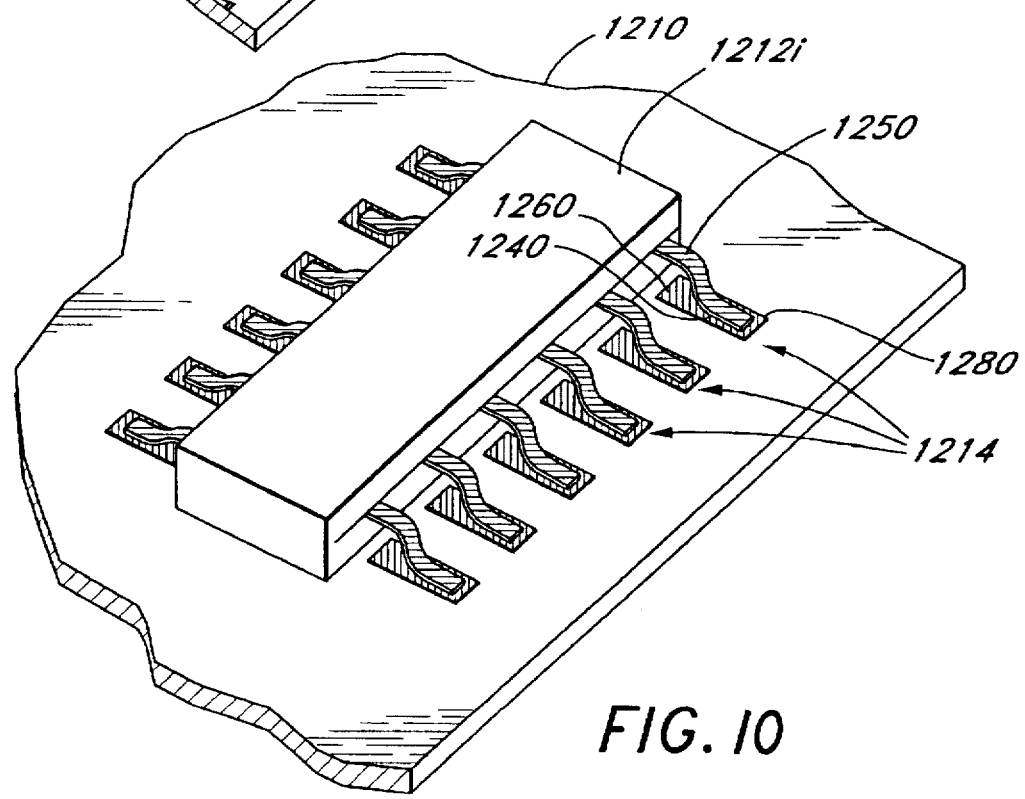
FIG. 10 shows a close-up of one of the electronic devices located on the circuit board in FIG. 9.

FIG. 10 shows a typical portion of the circuit board 1210 centered on the electronic device 1212i with emphasis on the electrical connections 1214 associated with the device 1212i. The illustrated electronic device 1212i is a surface mount technology device, often referred to as a small outline integrated circuit, soic. Device 1212i has a metal electrical lead shaped as a gull wing 1250. The gull wing metal electrical lead 1250 is attached to a metalized pad 1260 by means of a solder joint 1240. A pre-determined feature 1280, i.e., outer corner of metalized pad 1260, is in a typical location for a pre-determined feature to be located in the separate shadowgraph images. The location of the pre-determined feature 1280 is included in a CAD file which provides a detailed description of the circuit board 1210 and all of the components and solder connections thereon to the image analysis system 100 as previously discussed.

Shown in FIGS. 11a–11d are shadowgraph images of the electrical connection 1214 shown in FIG. 10 created by the four linear X-ray detectors 40, 50, 60, 70. The circuit board 1210 is oriented on the conveyor system 30 as shown in FIGS. 1–4 and 8 with the XYZ axes of the conveyor system aligned with the XYZ axes 1270 of the circuit board 1210 (see FIG. 9) aligned. FIG. 11a shows a shadowgraph image of the electrical connection 1214 created by the second linear X-ray detector 50. The solder joint 1240 forms an image 1240a; the gull wing metal electrical lead 1250 forms an image 1250a; the metalized pad 1260 forms an image 1260a; and the pre-determined feature 1280 forms an image 1280a. FIG. 11b shows a shadowgraph image of the electrical connection 1214 created by the first linear X-ray detector 40. The solder joint 1240 forms an image 1240b; the gull wing metal electrical lead 1250 forms an image 1250b; the metalized pad 1260 forms an image 1260b; and the pre-determined feature 1280 forms an image 1280b. FIG. 11c shows a shadowgraph image of the electrical connection 1214 created by the fourth linear X-ray detector 70. The solder joint 1240 forms an image 1240c; the gull wing metal electrical lead 1250 forms an image 1250c; the metalized pad 1260 forms an image 1260c; and the pre-determined feature 1280 forms an image 1280c. FIG. 11d shows a shadowgraph image of the electrical connection 1214 created by the third linear X-ray detector 60. The solder joint 1240 forms an image 1240d; the gull wing metal electrical lead 1250 forms an image 1250d; the metalized pad 1260 forms an image 1260d; and the pre-determined feature 1280 forms an image 1280d.

As shown in FIGS. 11a–11d, the images 1280a, 1280b, 1280c, 1280d of the pre-determined feature 1280 appears at various X and Y pixel values within the four shadowgraph views. For reference, the circuit board 1210 coordinate system 1270 is also shown. For clarity in understanding, one skilled in the art will recognize the images of a solder joint heel 1290a–1290d of solder joint 1240. Similar to the previous discussion of formation of the image of the arrow 562 in the laminographic cross sectional image 500 (see FIG. 7), each of the four shadowgraph images represented by FIGS. 11a–11d is shifted by a distance appropriate for each respective image in the X-direction and/or the Y-direction by a distance which causes the four images to substantially overlap one another thereby forming a reinforced image of the desired image plane.

In the present invention, the image analysis system 100 searches each of the four shadowgraph images for the images 1280a–1280d, respectively, of the pre-determined feature 1280. In the example shown in FIGS. 11a–11d, the pre-determined feature image 1280a is located at an X-axis pixel location of 2000 and a Y-axis pixel location of 3000 as shown in FIG. 11a; the pre-determined feature image 1280b is located at an X-axis pixel location of 2010 and a Y-axis pixel location of 3000 as shown in FIG. 11b; the pre-determined feature image 1280c is located at an X-axis pixel location of 2000 and a Y-axis pixel location of 2980 as shown in FIG. 11c; and the pre-determined feature image 1280d is located at an X-axis pixel location of 2010 and a Y-axis pixel location of 2980 as shown in FIG. 11d. It is important to note that these X-axis and Y-axis pixel locations are empirically determined, i.e., measured from the data (images) acquired by the system, as opposed to being determined from CAD data. (CAD data may be used to assist the analysis in determining the approximate general location of the pre-determined feature 1280, however, image analysis determines the precision locations given above.) Thus, if the circuit board is warped, i.e., different than the CAD data describing it, the warpage compensation is automatically included in the measurements. From these measurements, cross-sectional images of any desired plane relative the plane containing the pre-determined feature 1280 may be obtained. For example, in the simple case where the desired plane to be imaged is the same as the plane containing the pre-determined feature 1280, the cross-sectional image of this plane can be generated by the following pixel shifts of the shadowgraph images in FIGS. 11b, 11c and 11d with respect to FIG. 11a: a) FIG. 11a—no shift; b) FIG. 11b: X-shift=2000−2010=−10; Y-shift=3000−3000=0; c) FIG. 11c: X-shift=2000−2000=0; Y-shift=3000−2980=10; and d) FIG. 11d: X-shift=2000−2010=−10; Y-shift=3000−2980=10. Cross-sectional images of other planes which are not the same as the plane containing the pre-determined feature 1280 are likewise generated by an appropriate set of pixel shift factors which may be determined from a variety of other known geometrical factors. For example, the known geometrical factors may be obtained from the CAD data for the test object (circuit board); the geometrical configuration of the imaging system including the X-ray source, conveyor belt and detectors (system digital representation); image locations of multiple predetermined features at known relative locations in the test object (circuit board); etc. Thus, precision location and production of cross-sectional images at any desired plane of the test object (circuit board) can be produced independent of warpage in the test object (circuit board) and without the need to perform a separate Z-mapping with another measurement system such as a laser ranging system, etc. Furthermore, if a Z-map of the warpage or distortion in the test object (circuit board) is desired, it may also be generated using the above information.

FIG. 12 shows a flow diagram 1300 illustrating the process of automatic calculation of the warp compensation. In a first step 1310, the topographical Computer Aided Design (CAD) data and test parameters (digital representation of the imaging system) are recalled from the computer or image analysis system data memory. In a next step 1320, loop parameters are setup to loop calculations over all four shadowgraph images (FIGS. 11a–11d) of the test object, in this example circuit board 1210. In a next step 1330, loop parameters are setup to loop calculations over all N pre-determined features 1280 on the circuit board 1210. In a next step 1340, search start points and directions are defined based upon CAD data for board 1210 and for each pre-determined feature 1280. In a next step 1350, conventional image analysis routines and algorithms are used to locate both X and Y edges of each pre-determined feature 1280. Any of a multitude of well known and commonly used image analysis techniques may be used to locate the X and Y edges of the pre-determined features 1280. Note that other features besides edge locations may be used as pre-determined features, such as but not limited to, centroids or centers. Once the X and Y edges are found, a step 1360 records the following data in a warp compensation data array: X-Edge actual location; Y-Edge actual location; X-Edge-CAD location; Y-Edge-CAD location; Z-CAD-distance from a fixed reference surface, e.g., the surface of the circuit board; image number; and feature number. Many different array structures can be used to store the data for warpage compensation, depending upon the desired end result of the analysis and inspection. A next step 1370 determines if all pre-determined features on the board 1210, have been measured and if not loops back to step 1330 to complete the measurements. A next step 1380 determines if all four images of board 1210 have been analyzed for board warpage compensation and if not loops back to step 1320 to complete the analysis. A next step in the process 1390, completes the process of generation of warpage compensation factors, a warpage map, etc. for board 1210.

In summary, once the pixel locations of the images 1280a–1280d for each pre-determined feature 1280 within the test object (circuit board) have been determined, proper X and Y pixel offsets for each of the four shadowgraph images of the test object (circuit board) may be combined in such a way as to compensate for local warpage of the test object (circuit board). Additionally, the local warpage compensation factors may also be used to compensate the system for board skew as the board flows through the present invention of a continuous linear scanning laminography system according to the present invention or similar skewing which may occur in alternative design imaging systems.

While the discussion and examples contained herein have been with reference to four shadowgraph images (FIGS. 6a, 6b, 6c, 6d and FIGS. 11a, 11b, 11c, 11d), one skilled in the art will readily appreciate that the number of images analyzed is not critical to the practice of the present invention and will depend upon the requirements of the specific application of the invention and the type of imaging system employed. Thus, the principles of the present invention apply just as well to systems which employ more or less than 4 shadowgraph images.

It will be understood that the apparatus and method of the present invention for automatic warp compensation for continuous linear scan laminography may be embodied in other specific forms without departing from its spirit or essential characteristics. Thus, there are numerous other embodiments of the automatic warp compensation for continuous linear scan laminography system and method which will be obvious to one skilled in the art. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An electrical connection inspection device comprising:

a source of X-rays which emits X-rays through an electrical connection from a plurality of positions;

an X-ray detector system positioned to receive the X-rays produced by said source of X-rays which have penetrated the electrical connection, said X-ray detector system further comprising an output which emits data signals corresponding to an X-ray image of the electrical connection produced by the X-rays received and detected by said X-ray detector system after penetrating the electrical connection; and an analysis system comprising:

an image memory which stores said detector data signals thereby forming an image database which contains information sufficient to form a cross-sectional image of a cutting plane of the electrical connection; and an image processor which searches said image database for a specific pre-determined feature located at a first Z-axis level in the electrical connection and combines said detector data signals with reference to said first Z-axis level to form a specific Z-level image database which contains information sufficient to form a cross-sectional image of a cutting plane of the electrical connection at a second Z-axis level in the electrical connection.

2. A device as defined in claim 1 wherein said source of X-rays comprises a plurality of X-ray sources.

3. A device as defined in claim 1 wherein said X-ray detector system comprises a plurality of X-ray detectors.

4. A device as defined in claim 1 wherein said analysis system further comprises an image section which produces said cross-sectional image of a cutting plane of said electrical connection from said image database.

5. A device as defined in claim 1 wherein said first Z-axis level and said second Z-axis level are the same.

6. An inspection device comprising:

a source of penetrating radiation which emits radiation through a test object from a plurality of positions;

a detector system positioned to receive the radiation produced by said source of penetrating radiation which has penetrated the test object, said detector system further comprising an output which emits data signals corresponding to a penetrating radiation image of the test object produced by the radiation received and detected by said detector system after penetrating the test object; and an analysis system comprising:

an image memory which stores said detector data signals thereby forming an image database which contains information sufficient to form a cross-sectional image of a cutting plane of the test object; and an image processor which searches said image database for a specific pre-determined feature located at a first Z-axis level in the test object and combines said detector data signals with reference to said first Z-axis level to form a specific Z-level image database which contains information sufficient to form a cross-sectional image of a cutting plane of the test object at a second Z-axis level in the test object.

7. A device as defined in claim 6 wherein said source of penetrating radiation comprises a plurality of penetrating radiation sources.

8. A device as defined in claim 6 wherein said detector system comprises a plurality of detector systems.

9. A device as defined in claim 6 wherein said analysis system further comprises an image section which produces said cross-sectional image of a cutting plane of the test object at said second Z-axis level in the test object from said Z-level image database.

10. A method for inspecting an electrical connection comprising the steps of:

directing X-rays through the electrical connection from a plurality of positions;

detecting X-rays transmitted through the electrical connection from said plurality of positions with an X-ray detector system having an output which emits data signals corresponding to an X-ray image of the electrical connection produced by X-rays received and detected by said X-ray detector system after penetrating the electrical connection;

storing said X-ray detector data signals corresponding to said X-ray image of the electrical connection;

creating a database of information from said X-ray detector data signals which contains information sufficient to form a cross-sectional image of a cutting plane of the electrical connection;

searching said database of information for a specific pre-determined feature located at a first Z-axis level in the electrical connection; and combining said X-ray detector data signals with reference to said first Z-axis level to form a specific Z-level image database which contains information sufficient to form a cross-sectional image of a cutting plane of the electrical connection at a second Z-axis level in the electrical connection.

11. An apparatus for producing cross-sectional images of an object at a first Z-level of the object with reference to a second Z-level of the object comprising:

an imaging system for producing a first transmission shadowgraph image of the object from a first perspective and a second transmission shadowgraph image of the object from a second perspective, wherein said first transmission shadowgraph image includes an image of a specific pre-determined feature located at the second Z-level of the object and said second transmission shadowgraph image includes an image of the specific pre-determined feature located at the second Z-level of the object; and an image analysis system comprising:

an image memory which stores said first and second transmission shadowgraph images;

an image processor which searches said first and second transmission shadowgraph images for the images of the specific pre-determined feature located at the second Z-level of the object and combines said first and second transmission shadowgraph images with reference to the second Z-level of the object to form a cross-sectional image of the first Z-level of the object wherein the location of the first Z-level of the object is determined by reference to the location of the second Z-level of the object.

* * * * *